(12) United States Patent
Ferree et al.

(10) Patent No.: US 8,986,926 B2
(45) Date of Patent: Mar. 24, 2015

(54) COMPOSITIONS COMPRISING ORIENTED, IMMOBILIZED MACROMOLECULES AND METHODS FOR THEIR PREPARATION

(75) Inventors: Sean M. Ferree, Seattle, WA (US); Dwayne L. Dunaway, Seattle, WA (US)

(73) Assignee: NanoString Technologies, Inc., Seattle, WA (US)

(*) Notice: Subject to any disclaimer, the term of this patent is extended or adjusted under 35 U.S.C. 154(b) by 1460 days.

(21) Appl. No.: 11/645,270

(22) Filed: Dec. 22, 2006

(65) Prior Publication Data

US 2010/0261026 A1    Oct. 14, 2010

Related U.S. Application Data

(60) Provisional application No. 60/753,816, filed on Dec. 23, 2005.

(51) Int. Cl.
| | |
|---|---|
| *C12Q 1/68* | (2006.01) |
| *C12M 1/34* | (2006.01) |
| *C12M 3/00* | (2006.01) |
| *B82Y 5/00* | (2011.01) |
| *G01N 33/543* | (2006.01) |

(52) U.S. Cl.
CPC ............... *B82Y 5/00* (2013.01); *C12Q 1/6834* (2013.01); *C12Q 2565/513* (2013.01); *G01N 33/54353* (2013.01)
USPC .......................................... 435/6.1; 435/287.2

(58) Field of Classification Search
None
See application file for complete search history.

(56) References Cited

U.S. PATENT DOCUMENTS

| | | | | |
|---|---|---|---|---|
| 4,352,884 | A * | 10/1982 | Nakashima et al. | 435/180 |
| 5,707,797 | A * | 1/1998 | Windle | 435/6 |
| 5,750,343 | A * | 5/1998 | Maag et al. | 435/6 |
| 5,840,862 | A | 11/1998 | Bensimon et al. | |
| 5,871,918 | A * | 2/1999 | Thorp et al. | 435/6 |
| 6,001,983 | A | 12/1999 | Benner | |
| 6,054,327 | A | 4/2000 | Bensimon et al. | |
| 6,225,055 | B1 | 5/2001 | Bensimon et al. | |
| 6,265,153 | B1 | 7/2001 | Bensimon et al. | |
| 6,271,002 | B1 * | 8/2001 | Linsley et al. | 435/91.1 |
| 6,303,296 | B1 | 10/2001 | Bensimon et al. | |
| 6,344,319 | B1 | 2/2002 | Bensimon et al. | |
| 6,548,255 | B2 | 4/2003 | Bensimon et al. | |
| 6,824,974 | B2 * | 11/2004 | Pisharody et al. | 435/4 |

(Continued)

FOREIGN PATENT DOCUMENTS

| | | |
|---|---|---|
| JP | 2004-125601 A | 4/2004 |
| JP | 2005-087057 A | 4/2005 |

(Continued)

OTHER PUBLICATIONS

Washizu et al, IEEE Transaction of Industry Applications, vo. 31, pp. 447-456 (1995).*

(Continued)

*Primary Examiner* — Robert T. Crow
(74) *Attorney, Agent, or Firm* — Cooley LLP; Ivor R. Elrifi; Matthew Pavao

(57) ABSTRACT

The present invention provides methods and compositions that facilitate the identification of structures of a variety of macromolecules. For instance, the present invention provides methods for the selective immobilization of macromolecules in an extended or oriented state. The present invention also provides compositions comprising macromolecules selectively immobilized in extended or oriented states.

39 Claims, 8 Drawing Sheets

(56) References Cited

U.S. PATENT DOCUMENTS

| | | | |
|---|---|---|---|
| 2003/0027201 A1* | 2/2003 | Schwartz | 435/6 |
| 2003/0143549 A1* | 7/2003 | Yang et al. | 435/6 |
| 2003/0175779 A1* | 9/2003 | Bensimon et al. | 435/6 |
| 2004/0023205 A1 | 2/2004 | Ladner et al. | |
| 2004/0077090 A1 | 4/2004 | Short | |
| 2004/0086892 A1* | 5/2004 | Crothers et al. | 435/6 |
| 2005/0274612 A1* | 12/2005 | Segawa et al. | 204/403.01 |

FOREIGN PATENT DOCUMENTS

| | | | |
|---|---|---|---|
| JP | 2005-249739 A | 9/2005 | |
| JP | 2006-503297 A | 1/2006 | |
| WO | WO-0113088 A1 | 2/2001 | |
| WO | WO 03003810 A2 * | 1/2003 | |
| WO | WO 2004/036591 A1 | 4/2004 | |

OTHER PUBLICATIONS

Chi-Han Chiou et al. "A micromachined DNA manipulation platform for the stretching and rotation of a single DNA molecule." Journal of Micromechanics and Microengineering. 15 (1): 109-117. (2005).

Ferree et al. "The Hydrodynamics of DNA Electrophoretic Stretch and Relaxation in a Polymer Solution." Biophysical Journal. 87(1): 468-475. (2004).

Wang et al. "Stretching DNA with Optical Tweezers." Biophysical Journal. 72(3): 1335-1346. (1997).

Bier et al. "Oriented Immobilization of Single DNA Molecules as a Nanostring Tool." *AIP Conf. Proc.* 640(2002):51-59.

Gu et al. "DNA Nanowire Fabrication." *Nanotechnology.* 17(2006):R14-R25.

Kim et al. "DC Electric-Field-Induced DNA Stretching for AFM and SNOM Studies." *Ultramicroscopy.* 91(2002):139-149.

Namasivayam, V et al, "Electrostretching DNA molecules using polymer-enhanced media within microfabricated devices", *Anal Chem.*, 74, pp. 3378-3385, 2002.

Asbury et al, "Trapping of DNA by dielectrophoresis", *Electrophoresis*, 23(16):2658-2666 (2002).

Asbury et al., "Trapping of DNA in nonuniform oscillating electric fie", *Biophys. J.*, 74:1024-1030 (1998).

Ashkin et al., "Optical trapping and manipulation of single cells using infrared laser beams", *Nature*, 330:769-771 (1987).

Ashkin et al., "Observation of a single-beam gradient force optical trap for dielectric particles", *Opt. Lett.*, 11:288-290 (1986).

Ashkin et al., "Optical trapping and manipulation of viruses and bacteria", *Science*, 235:1517-1520 (1987).

Bensimon et al., "Alignment and sensitive detection of DNA by a moving interface", *Science*, 265:2096-2098 (1994).

Block et al., "Bead movement by single kinesin molecules studied with optical tweezers", *Nature*, 348:348-352 (1990).

Egholm et al., "Peptide Nucleic Acids (PNA). Oligonucleotide Analogues with an Achiral Peptide Backbone", *J. Am. Chem. Soc.*, 114:1895-1897 (1992).

Ferree et al., "Electrokinetic stretching of tethered DNA", *Biophys. J.*, 85(4):2539-2546 (2003).

Goodchild, J., "Conjugates of oligonucleotides and modified oligonucleotides: a review of their synthesis and properties", *Bioconjugate Chem.*, 1(3):165-187 (1990).

Grier, D. G., "A revolution in optical manipulation", *Nature*, 424:810-816 (2003).

Gryaznov et al., "Okigodeoxyribonucleotide N3'→P5' Phosphoramidates: Synthesis and Hybridization Properties", *J. Am. Chem. Soc.*, 116:3143-3144 1994.

Henegariu et al., "Rapid DNA fiber technique for size measurements of linear and circular DNA probes", BioTech., 31:246-250 (2001).

Kabata et al., "Visualization of single molecules of RNA polymerase sliding along DNA", *Science*, 262(5139):1561-1563 (1993).

Kraus et al., "High-resolution comparative hybridization to combed DNA fibers", *Human Genet.*, 99:374-380 (1997).

Matsuura et al., "One-end immobilization of individual DNA molecules on a functional hydrophobic glass surface", *J. Biomol. Struct. Dyn.*, 20(3):429-436 (2002).

Matsuura et al., "Real-time observation of a single DNA digestion by lambda exonuclease under a fluorescence microscope field", *Nucl. Acids Res.*, 29(16):E79 (2001).

Michalet et al., "Dynamic molecular combing: stretching the whole human genome for high-resolution studies", *Science*, 277:1518-1523 (1997).

Otobe et al., "Behavior of DNA fibers stretched by precise meniscus motion control", *Nucl. Acids Res.*, 29:E109 (2001).

Pease et al., "Light-generated oligonucleotide arrays for rapid DNA sequence analysis", *Proc. Natl. Acad. Sci. U.S.A.*, 91:5022-5026 (1994).

Perkins et al., "Relaxation of a single DNA molecule observed by optical microscopy", *Science*, 264:822-826 (1994).

Simmons et al., "Quantitative measurements of force and displacement using an optical trap", *Biophys. J.*, 70:1813-1822 (1996).

Stigter et al., "Theory for the hydrodynamic and electrophoretic stretch of tethered B-DNA", *Biophys. J.*, 75(3):1197-1210 (1998).

Uhlman et al., "Antisense Oligonucleotides: A New Therapeutic Principle", *Chem. Rev.*, 90(4):544-584 (1990).

Yokota et al., "A new method for straightening DNA molecules for optical restriction mapping", *Nucl. Acids Res.*, 25(5):1064-1070 (1997).

Zimmermann et al., "DNA stretching on functionalized gold surfaces", *Nucl. Acids Res.*, 22(3):492-497 (1994).

* cited by examiner

FIG. 6A
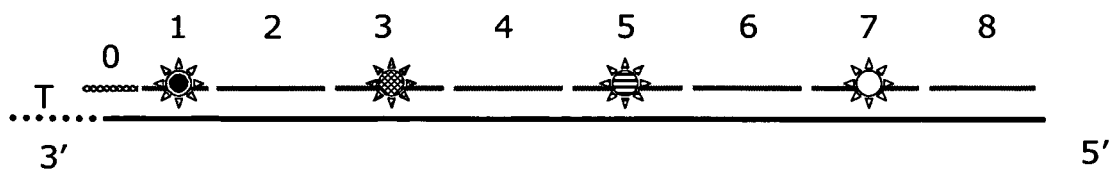
FIG. 6B
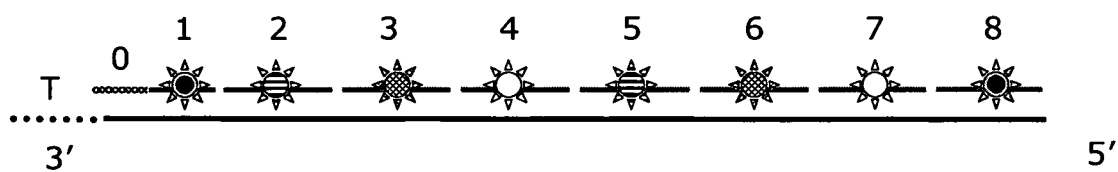
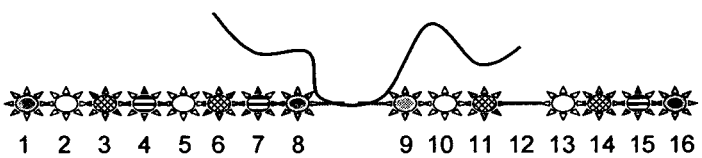
FIG. 7A
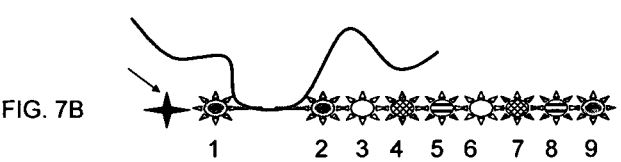
FIG. 7B
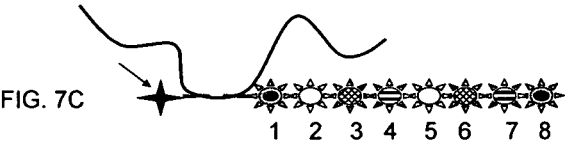
FIG. 7C FIG. 8A
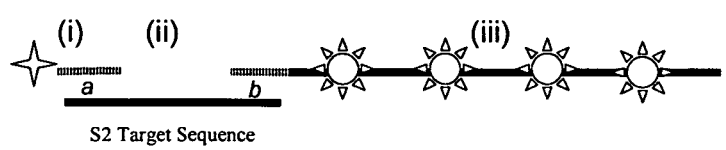
S2 Target Sequence
FIG. 8E
FIG. 8B
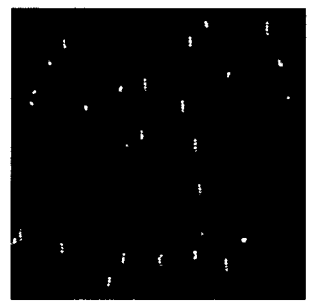
FIG. 8C
FIG. 8D

COMPOSITIONS COMPRISING ORIENTED, IMMOBILIZED MACROMOLECULES AND METHODS FOR THEIR PREPARATION

This application claims benefit under 35 U.S.C. §119(e) of U.S. Provisional Application No. 60/753,816, filed Dec. 23, 2005, which is incorporated by reference herein in its entirety.

1. FIELD OF THE INVENTION

The present invention relates to the fields of macromolecular recognition, macromolecular labeling, macromolecular stretching, macromolecular orientation, macromolecular immobilization and nanotechnology.

2. BACKGROUND OF THE INVENTION

Macromolecules can comprise unique sequences of monomers or other moieties that can be used to readily distinguish one macromolecule from another. When a macromolecule is bound to or associated with another entity, that entity can be identified by features of the macromolecule. The entity can be any entity apparent to one to those of skill in the art such as a substrate, a surface, another molecule, a position in an array or any other entity with which a macromolecule can be associated. One can readily identify the entity by identifying the macromolecule.

Of the many features of macromolecules, their structure provides much of their diversity. Generally, their primary structure, i.e. the sequence of their monomers or other moieties, distinguishes one macromolecule from another macromolecule. However, many, if not most, macromolecules comprise further levels of structure, such as secondary, tertiary or even quaternary structure, that can actually hinder the ability of one of skill to identify the primary structure of the macromolecule. To illustrate, a simple macromolecule comprising a primary sequence of features A, B, C, D, E and F can be readily identified if each feature can be recognized one after the other along the primary sequence. However, if that macromolecule were twisted, kinked or folded into a three dimensional structure, as is often the case with naturally occurring macromolecules in solution, the features might not be readily identifiable in their proper sequence. One of skill in the art might not be able to distinguish a macromolecule having the primary structure A, B, F, C, E and D from the primary structure A, B, C, D, E and F due to secondary or tertiary or quaternary structure.

Persons of skill have developed techniques to tease primary structure out of a three dimensional macromolecule. For certain macromolecules, e.g. polynucleotides and polypeptides, chemical techniques for identifying the primary sequence of their features will be familiar to those of skill. In addition, a few techniques for extending or stretching or combing macromolecules have been developed to reduce the complexity of their structures and thereby facilitate the elucidation of primary structure. These techniques have generally involved the application of some force capable of extending the macromolecule. Some techniques have further involved the nonselective fixing of the macromolecule in an extended state, for instance by drying the macromolecule on a surface.

Methods and compositions that facilitate the identification of the primary structure of a macromolecule will further enhance their utility in the fields of macromolecular recognition and macromolecular labeling and other fields.

3. SUMMARY OF THE INVENTION

The present invention provides methods and compositions that facilitate the identification of primary structures of a variety of macromolecules. In certain aspects, the present invention provides methods for the selective immobilization of macromolecules in an extended state. Remarkably, according to the invention, a macromolecule can be selectively immobilized while fully extended under whatever force is used for the extension. In addition, the methods of the invention facilitate the selective immobilization of extended macromolecules that are oriented with respect to each other. In other words, according to the methods of the invention, a plurality of macromolecules can readily be immobilized in the same orientation with respect to each other.

In one aspect, the present invention provides methods for selectively immobilizing a macromolecule in an extended state. The macromolecule can be any macromolecule known to those of skill in the art such as a polymer, a polysaccharide, a polynucleotide or a polypeptide. For the methods of this aspect of the invention, generally, a first portion of the macromolecule is immobilized by any technique known to those of skill in the art. Indeed, the technique for immobilizing the first portion of the macromolecule is not critical to many embodiments of the invention. In certain embodiments, the first portion of the macromolecule can be immobilized selectively or non-selectively. In certain embodiments the first portion is immobilized by one or more covalent bonds. In certain embodiments, the first portion is immobilized by one or more non-covalent bonds. Exemplary immobilized first portions are described in the sections below.

With an immobilized first portion, the macromolecule can be extended by any technique for extending a macromolecule apparent to those of skill in the art. In certain embodiments, the technique for extending the macromolecule is not critical for the methods of the invention. In certain embodiments, the technique for extending the macromolecule appropriate for the class of macromolecule according to the judgment of one of skill in the art. In certain embodiments, the macromolecule is extended by application of a force capable of extending the macromolecule. The force can be any force apparent to one of skill in the art for extending the macromolecule. Exemplary forces include gravity, hydrodynamic force, electromagnetic force and combinations thereof. Specific techniques for extending the macromolecule are described in the sections below.

The macromolecule is in an extended state if it would be recognized as extended by one of skill in the art. In certain embodiments, the macromolecule is in an extended state when it is in the field of a force capable of extending the macromolecule. In certain embodiments, the macromolecule is in an extended state when its average hydrodynamic radius is more than double the average hydrodynamic radius of the macromolecule in its native state as recognized by those of skill in the art.

In this aspect of the invention, the methods generally comprise the step of selectively immobilizing a second portion of the macromolecule while it is in an extended state. This can result in an immobilized macromolecule that is extended between the first and the second portion. Remarkably, since the macromolecule is selectively immobilized while extended, that extension can be preserved in the immobilized macromolecule. Generally, the first portion and the second portion of the macromolecule are not the same.

The selective immobilization can be according to any technique for selective immobilization of a portion of a macromolecule apparent to those of skill in the art. The selective immobilization can be through, for example, the formation of one or more covalent bonds or one or more non-covalent bonds, or both. Particular examples of selective immobilization techniques are described in the sections below. In particular embodiments, one or more binding pairs are used to immobilize the second portion of the macromolecule.

The second portion can be immobilized onto any substrate apparent to those of skill in the art. The substrate can be any substrate judged to be useful for immobilization known to those of skill in the art. In certain embodiments, the second portion can be immobilized to another molecule. Further useful substrates include surfaces, membranes, beads, porous materials, electrodes, arrays and any other substrate apparent to those of skill in the art.

In another aspect, the present invention provides compositions comprising a selectively immobilized, extended macromolecule. The compositions generally comprise a substrate and an extended macromolecule selectively immobilized onto the substrate. The substrate can be any substrate known to those of skill in the art. Exemplary substrates include those described in the sections below. At least two portions of the macromolecule are immobilized onto the substrate, and the macromolecule is in an extended state between the two portions. In certain embodiments, at least one portion of the macromolecule is selectively immobilized onto the substrate. In certain embodiments, two or more portions of the macromolecule are selectively immobilized onto the substrate. The macromolecule can be extended and/or immobilized by any technique apparent to those of skill, including particularly the methods of the present invention.

In another aspect, the present invention provides methods for selectively immobilizing a macromolecule in an oriented state. The macromolecule can be any macromolecule described above. In certain embodiments, the macromolecule can be flexible, or in certain embodiments the macromolecule can be rigid or semi-rigid. For the methods of this aspect of the invention, generally, a first portion of the macromolecule is immobilized as described above. With an immobilized first portion, the macromolecule can be oriented by any technique for extending a macromolecule apparent to those of skill in the art. In certain embodiments, the technique for orienting the macromolecule is not critical for the methods of the invention. In certain embodiments, the technique for orienting the macromolecule appropriate for the class of macromolecule according to the judgment of one of skill in the art. In certain embodiments, the macromolecule is oriented by application of a force capable of orienting the macromolecule. The force can be any force apparent to one of skill in the art for orienting the macromolecule. Exemplary forces include gravity, hydrodynamic force, electromagnetic force and combinations thereof. Specific techniques for extending the macromolecule are described in the sections below.

The macromolecule is in an oriented state if it would be recognized as oriented by one of skill in the art. In certain embodiments, the macromolecule is in an oriented state when it is in the field of a force capable of orienting the macromolecule. In certain embodiments, the macromolecule is in an oriented state when its termini are arranged in parallel, as recognized by those of skill in the art, with the field of a force capable of orienting the macromolecule. In certain embodiments, a plurality of macromolecules is in an oriented state when the termini of the macromolecules are arranged in parallel, as recognized by those of skill in the art.

In this aspect of the invention, the methods generally comprise the step of selectively immobilizing a second portion of the macromolecule while it is in an oriented state. This can result in an immobilized macromolecule that is oriented between the first and the second portion. Remarkably, since the macromolecule is selectively immobilized while extended, that orientation can be preserved in the immobilized macromolecule. The selective immobilization can according to the methods described above.

In another aspect, the present invention provides a compositions comprising a selectively immobilized, oriented macromolecule. The compositions generally comprise a substrate and an oriented macromolecule selectively immobilized onto the substrate. The substrate can be any substrate known to those of skill in the art. Exemplary substrates include those described in the sections below. At least two portions of the macromolecule are immobilized onto the substrate, and the macromolecule is in an oriented state between the two portions. In certain embodiments, at least one portion of the macromolecule is selectively immobilized onto the substrate. In certain embodiments, both portions of the macromolecule are selectively immobilized onto the substrate. The macromolecule can be oriented and/or immobilized by any technique apparent to those of skill, including particularly the methods of the present invention.

The methods and compositions of the present invention can be used for any purpose apparent to those of skill in the art. For instance, the immobilized and extended and/or oriented macromolecule can be used as a label for a substrate on which the macromolecule is immobilized. The primary sequence of the immobilized and extended and/or oriented macromolecule can be identified by any technique apparent to those of skill. Advantageously, immobilization of the extended and/or oriented macromolecule can facilitate such techniques. In certain embodiments, the immobilized and extended and/or oriented macromolecule can be used to guide the manufacture of nanopaths, for example to create nanowires or nanocircuits. Further uses for the immobilized and extended and/or oriented macromolecules are described in the sections below.

4. BRIEF DESCRIPTION OF THE FIGURES

FIG. 1A provides an illustration of a macromolecule comprising an immobilized first portion F1;

FIG. 1B provides an illustration of a macromolecule extended in an electrical field and comprising immobilized first portion F1 and immobilized second portion F2, wherein F2 is immobilized via a complex with molecule F3;

FIG. 2A provides an illustration of a three-member complex for immobilization of an extended macromolecule;

FIG. 2B provides an illustration of a two-member complex for immobilization of an extended macromolecule;

FIG. 2C provides an illustration of an incomplete complex for immobilization of an extended macromolecule;

FIG. 3A provides an illustration of a macromolecule comprising an immobilized first portion F1;

FIG. 3B provides an illustration of an extended macromolecule immobilized at first portion F1 and at a second portion via complexes with F2;

FIG. 3C provides an illustration of a macromolecule comprising a first portion immobilized to an avidin surface via biotin;

FIG. 3D provides an illustration of an extended macromolecule immobilized at a first portion and at a second portion via selective binding of biotin to an avidin surface;

Figure 5:
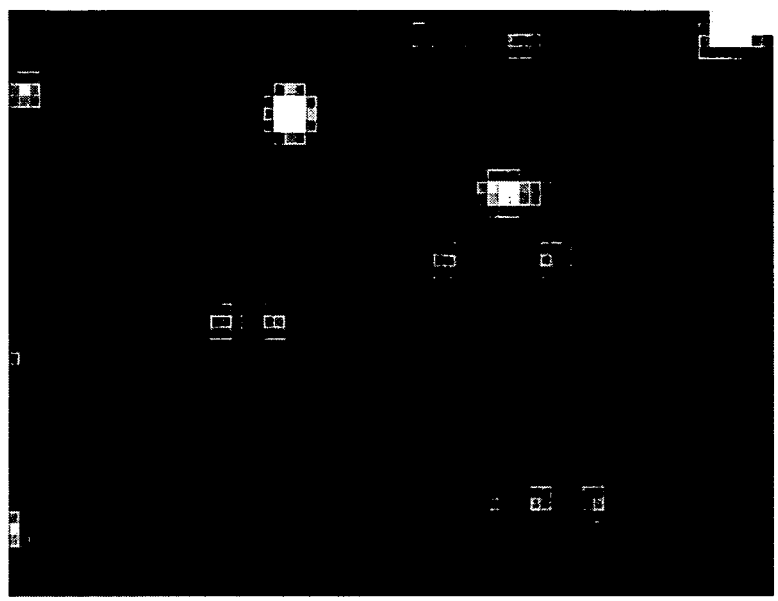

FIG. 5 provides an image of extended macromolecules selectively immobilized by the methods of the present invention;

FIG. 6A provides a nanoreporter in which alternate spots are labeled;

FIG. 6B depicts a nanoreporter in which every spot is labeled;

FIG. 7A illustrates a dual nanoreporter with a 16-position nanoreporter code, using two 8-position nanoreporter components;

FIG. 7B illustrates a dual nanoreporter with a 9-position nanoreporter code;

FIG. 7C illustrates a dual nanoreporter with an 8-position nanoreporter code, using one ghost probe and one 8-position nanoreporter component;

FIG. 8A provides a schematic illustration of the experiment shown in FIGS. 6B and 6C where the star represents biotin that was used to attach the complex by one end to the surface prior to stretching;

FIGS. 8B and 8C provide images from experiments in which S2-A ghost probe, S2-B labeled nanoreporter and S2 target DNA (FIG. 8B) or S2 target RNA (FIG. 8C) were hybridized;

FIG. 8D provides an image of a negative control experiment, in which S2-A ghost probe, S2-B labeled nanoreporter and no S2 target RNA were hybridized; and FIG. 8E provides a close-up of a nanoreporter complexes from FIG. 8B.

5. DETAILED DESCRIPTION OF THE INVENTION

5.1 Definitions

All terms used herein have their ordinary meanings to those of skill in the art unless indicated otherwise. The following terms shall have the following meanings.

As used herein, the term "binding pair" refers to first and second molecules or moieties that are capable of selectively binding to each other, i.e. binding to each other with greater affinity than to other components in a composition. The binding between the members of the binding pair can be covalent or non-covalent. In certain embodiments, the binding is non-covalent. Exemplary binding pairs include immunological binding pairs (e.g. any haptenic or antigenic compound in combination with a corresponding antibody or binding portion or fragment thereof, for example digoxigenin and anti-digoxigenin, fluorescein and anti-fluorescein, dinitrophenol and anti-dinitrophenol, bromodeoxyuridine and anti-bromodeoxyuridine, mouse immunoglobulin and goat anti-mouse immunoglobulin) and nonimmunological binding pairs (e.g., biotin-avidin, biotin-streptavidin, hormone-hormone binding protein, receptor-receptor ligand (e.g., acetylcholine receptor-acetylcholine or an analog thereof), IgG-protein A, lectin-carbohydrate, enzyme-enzyme cofactor, enzyme-enzyme inhibitor, complementary polynucleotide pairs capable of forming nucleic acid duplexes, and the like). For instance, immunoreactive binding members may include antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other binding members. Other common binding pairs include but are not limited to, biotin and avidin (or derivatives thereof), biotin and streptavidin, carbohydrates and lectins, complementary nucleotide sequences (including probe and capture nucleic acid sequences), complementary peptide sequences including those formed by recombinant methods, effector and receptor molecules, hormone and hormone binding protein, enzyme cofactors and enzymes, enzyme inhibitors and enzymes, and so forth.

"Selective binding" refers to the any preferential binding of a pair of molecules or moieties for each other with respect to other molecules or moieties in a composition that would be recognized by one of skill in the art. In certain embodiments, a pair of molecules or moieties selectively binds when they preferentially bind each other compared to other molecules or moieties. Selective binding can include affinity or avidity, or both, of one molecule or moiety for another molecule or moiety. In particular embodiments, selective binding requires a dissociation constant ($K_D$) of less than about $1\times10^{-5}$ M or less than about $1\times10^{-6}$ M, $1\times10^{-7}$ M, $1\times10^{-8}$ M, $1\times10^{-9}$ M, or $1\times10^{-10}$ M. In contrast, in certain embodiments, non-selective binding has significantly less affinity, for example, a $K_D$ greater than $1\times10^{-3}$ M.

"Extended state" refers to a macromolecule in a state that would be recognized as extended by one of skill in the art. In certain embodiments, a macromolecule is in an extended state when it is extended relative to its native conformation in solution. In certain embodiments, a macromolecule is in an extended state when it is in the field of a force capable of extending the macromolecule. In certain embodiments, an extended state of a macromolecule can be determined quantitatively. In such embodiments, those of skill in the art will recognize R as the end-to-end vector of the macromolecule, i.e. the distance between two termini of the macromolecule, and <R> as the average end-to-end vector such that 95% of R will be within 2<R> in a solution deemed appropriate to one of skill in the art. Exemplary solutions include, for example, a dilute solution of the macromolecule in water or in a pH buffer. In particular embodiments, a macromolecule is in an extended state when R is greater than 2.0<R>.

"Oriented state" refers to a macromolecule in a state that would be recognized as oriented by one of skill in the art. In certain embodiments, a macromolecule is in an oriented state when it is oriented relative to its native conformation in solution. In certain embodiments, the macromolecule is oriented when it is arranged in parallel with the field of a force capable of orienting the macromolecule. In certain embodiments, the macromolecule is oriented when it is one of a plurality of macromolecules that are arranged in parallel, as recognized by those of skill in the art.

5.2 Methods of Selective Immobilization

As described in the summary, the present invention provides methods for the selective immobilization of a macromolecule in an extended state. The macromolecule, once selectively immobilized, can be used for any purpose apparent to those of skill in the art.

5.2.1 Macromolecules

In the methods, the macromolecule can be any macromolecule known to those of skill in the art without limitation. In certain embodiments, the macromolecule is a macromolecule that is capable of being extended in the methods of the invention. In certain embodiments, the macromolecule is capable of being immobilized in one or two portions as described in the sections below.

In certain embodiments, the macromolecule is any polymer known to those of skill in the art. For instance, the macromolecule can be a polysaccharide, a polypeptide or a polynucleotide. Useful polynucleotides include ribonucleic acids, deoxyribonucleic acids and other polynucleotides known to those of skill in the art.

The macromolecule can be of any size that is sufficient to allow extension and immobilization of the macromolecule according to the methods of the invention. In certain embodiments when the macromolecule is a polynucleotide, the macromolecule can have a length of greater than 500 bp, greater than 750 bp, greater than 1 kb, greater than 1.5 kb, greater than 2.0 kb, greater than 2.5 kb, greater than 3.0 kb, greater than 4.0 kb or greater than 5.0 kb. In certain embodiments, when the macromolecule is a polypeptide, the macromolecule can have a size of greater than 50 amino acids, greater than 100 amino acids, greater than 200 amino acids, greater than 300 amino acids, greater than 400 amino acids, greater than 500 amino acids, greater than 750 amino acids, greater than 1000 amino acids, greater than 1500 amino acids, greater than 2000 amino acids, greater than 2500 amino acids, greater than 3000 amino acids, greater than 4000 amino acids or greater than 5000 amino acids. In certain embodiments, when the macromolecule is a polysaccharide, the macromolecule can have a size of greater than 50 saccharides, greater than 100 saccharides, greater than 200 saccharides, greater than 300 saccharides, greater than 400 saccharides, greater than 500 saccharides, greater than 750 saccharides, greater than 1000 saccharides, greater than 1500 saccharides, greater than 2000 saccharides, greater than 2500 saccharides, greater than 3000 saccharides, greater than 4000 saccharides or greater than 5000 saccharides.

The macromolecule can be a native macromolecule as understood by those of skill in the art, or the macromolecule can be a non-native macromolecule. In certain embodiments, when the macromolecule is a polypeptide, the macromolecule can comprise only naturally occurring amino acids, or the macromolecule can comprise naturally occurring amino acids and non-naturally occurring amino acids. The other amino acids can be any amino acids, or derivatives or analogs thereof, known to those of skill in the art. In certain embodiments, when the macromolecule is a polynucleotide, the polynucleotide can comprise only naturally occurring nucleotides, or the polynucleotide can comprise naturally occurring nucleotides and non-naturally occurring nucleotides. In certain embodiments, when the macromolecule is a polysaccharide, the polysaccharide can comprise only naturally occurring saccharides, or the polysaccharide can comprise naturally occurring saccharides and non-naturally occurring saccharides. In certain embodiments, the polymers can comprise only non-natural monomers. In further embodiments, the macromolecule can comprise a plurality of classes of monomers, such as amino acids, nucleotides and/or saccharides.

Figure 2A:
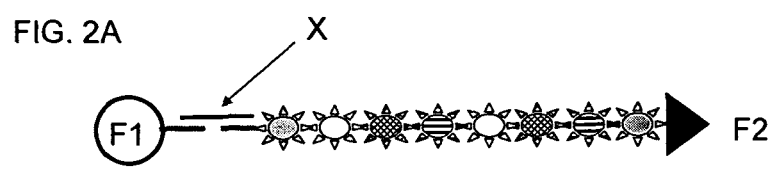

In certain embodiments, the macromolecule comprises only one primary, covalently linked chain of monomers. For instance, when the macromolecule is a polypeptide, in certain embodiments, the macromolecule comprises only one primary amino acid chain. When the macromolecule is a polynucleotide, in certain embodiments, the macromolecule is single stranded. In further embodiments, the macromolecule comprises two primary, covalently linked chains of monomers. For instance, when the macromolecule is a polypeptide, in certain embodiments, the macromolecule comprises two primary amino acid chains. When the macromolecule is a polynucleotide, in certain embodiments, the macromolecule comprises two polynucleotide strands; in certain embodiments, the macromolecule can be double stranded, in part or in whole. In further embodiments, the macromolecule comprises three or more primary, covalently linked chains of monomers. For instance, when the macromolecule is a polypeptide, in certain embodiments, the macromolecule comprises three primary amino acid chains. When the macromolecule is a polynucleotide, in certain embodiments, the macromolecule comprises three polynucleotide strands. For instance, the macromolecule can comprise three strands F1, X and F2 where a portion of strand X is complementary to strand F1 and a portion of strand X is complementary to strand F2. An example is illustrated in FIG. 2A. In certain embodiments, the macromolecule comprises more than three primary, covalently linked chains of monomers.

Advantageously, a macromolecule of the invention can comprise one or more labels that facilitate the detection, imaging or identification of the macromolecule by techniques known to those of skill in the art. The label can be any detectable moiety known to those of skill in the art. Exemplary labels for macromolecules include detectable isotopes, radioisotopes, fluors, dyes, enzymes, ligands, receptors, antigens, antibodies, lectins, carbohydrates, nucleotide sequences, and any other detectable label apparent to those of skill in the art. Useful labels, macromolecules comprising labels, and methods of their preparation are described in U.S. provisional application No. 60/753,758, filed Dec. 23, 2005, entitled "Nanoreporters And Methods Of Manufacturing And Use Thereof," the contents of which are hereby incorporated by reference in their entirety.

In certain embodiments, a polynucleotide is a polymer of natural (e.g. A, G, C, T, U) or synthetic nucleobases, or a combination of both. The backbone of the polynucleotide can be composed entirely of "native" phosphodiester linkages, or it may contain one or more modified linkages, such as one or more phosphorothioate, phosphorodithioate, phosphoramidate or other modified linkages. As a specific example, a polynucleotide may be a peptide nucleic acid (PNA), which contains amide interlinkages. Additional examples of synthetic bases and backbones that can be used in conjunction with the invention, as well as methods for their synthesis can be found, for example, in U.S. Pat. No. 6,001,983; Uhlman & Peyman, 1990, *Chemical Review* 90(4):544 584; Goodchild, 1990, *Bioconjugate Chem.* 1(3):165 186; Egholm et al., 1992, *J. Am. Chem. Soc.* 114:1895 1897; Gryaznov et al., *J. Am. Chem. Soc.* 116:3143 3144, as well as the references cited in all of the above. Common synthetic nucleobases of which polynucleotides may be composed include 3-methlyuracil, 5,6-dihydrouracil, 4 thiouracil, 5 bromouracil, 5-thorouracil, 5-iodouracil, 6-dimethyl aminopurine, 6-methyl aminopurine, 2-aminopurine, 2,6-diamino purine, 6-amino-8-bromopurine, inosine, 5-methylcytosine, 7-deazaadenine, and 7-deazaguanosine. Additional non-limiting examples of synthetic nucleobases of which the target nucleic acid may be composed can be found in Fasman, *CRC Practical Handbook of Biochemistry and Molecular Biology*, 1985, pp. 385-392; *Beilstein's Handbuch der Organischen Chemie*, Springer Verlag, Berlin and Chemical Abstracts, all of which provide references to publications describing the structures, properties and preparation of such nucleobases.

The macromolecule can be prepared according to any technique apparent to those of skill in the art. Advantageously, macromolecules according to the invention can comprise labels and/or members of binding pairs, as described in the sections below, that can be used to facilitate preparation and/or purification of the macromolecule. In addition, certain macromolecules of the invention are capable of forming complexes with molecules that comprise members of binding pairs, as described below. These complexes can be used to facilitate preparation and/or purification of the macromolecule or complex.

5.2.2 Immobilization of First Portion

In the methods of the invention, a first portion of the macromolecule is immobilized. Generally, the first portion is immobilized if it would be recognized as immobilized by one of skill in the art. The first portion can be immobilized by any technique apparent to those of skill in the art. In certain embodiments, the technique for immobilization of the first portion of the macromolecule is not critical for the methods of the invention.

The first portion of the macromolecule can be at any location in the macromolecule. In certain embodiments, the first portion is at a terminus of the macromolecule. For the purposes of the invention, a portion of a macromolecule can be "at a terminus" when it is less than five, four, three, two, one or zero monomers from a terminus of the macromolecule. Of course, although many macromolecules have two termini, the methods of the invention are applicable to macromolecules have more than two termini and to macromolecules having one or zero termini, e.g. circular macromolecules. In certain embodiments, the first portion is not at a terminus of the macromolecule.

The macromolecule can be immobilized onto any substrate apparent to those of skill in the art. The substrate can be any moiety to which the macromolecule can be immobilized without limitation. In certain embodiments, the substrate is a surface, membrane, bead, porous material, electrode or array.

In certain embodiments, the first portion of the macromolecule can be immobilized non-selectively. In further embodiments, the first portion of the macromolecule can be immobilized selectively. In advantageous embodiments, after the first portion of the macromolecule is immobilized, some portion of the macromolecule should be free to move sufficiently so that the macromolecule can be extended and/or oriented in following steps of the method. In particular, in certain embodiments, when the first portion of the macromolecule is immobilized non-selectively, it is important that the entire macromolecule not be immobilized non-selectively to an extent that prevents extension of any portion of the macromolecule.

The immobilization can be by any interaction with the substrate apparent to those of skill in the art. The immobilization can be via electrostatic or ionic interaction, via one or more covalent bonds, via one or more non-covalent bonds or combinations thereof. In certain embodiments, the immobilization can be via electrostatic interaction with an electrode. In further embodiments, the immobilization is via electrostatic interaction with a substrate other than the electrode.

Figure 1A:
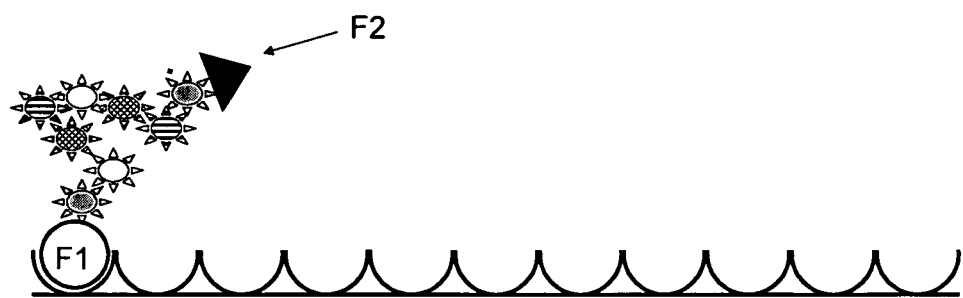

In certain embodiments, the first portion of the macromolecule comprises a first member of a binding pair. The first member of the binding pair can be covalently bound to the first portion of the macromolecule, or they can be non-covalently bound. Useful covalent bonds and non-covalent bonds will be apparent to those of skill in the art. In useful embodiments, the substrate onto which the first portion of the macromolecule is bound will comprise a second member of the binding pair. The substrate can be covalently bound to the second member, or they can be non-covalently bound. FIG. 1A illustrates a macromolecule that comprises a moiety F1 that is capable of selectively binding a moiety of the substrate. Moiety F1 can be, for example, biotin, capable of binding, for example, a substrate coated with avidin.

In certain embodiments, the first portion of the macromolecule can comprise a member of a binding pair that is capable of binding with a member of a binding pair on the substrate to form one or more non-covalent bonds. Exemplary useful substrates include those that comprise a binding moiety selected from the group consisting of ligands, antigens, carbohydrates, nucleic acids, receptors, lectins, and antibodies. The first portion of the macromolecule would comprise a binding moiety capable of binding with the binding moiety of the substrate.

In advantageous embodiments, the first portion of the macromolecule can be immobilized to the substrate via an avidin-biotin binding pair. In certain embodiments, the macromolecule can comprise a biotin moiety in its first portion. For instance, a polynucleotide macromolecule can comprise a biotinylated nucleotide residue. Similarly, a polypeptide macromolecule can comprise a biotinylated amino acid residue. The substrate comprising avidin can be any substrate comprising avidin known to those of skill in the art. Useful substrates comprising avidin are commercially available including TB0200 (Accelr8), SAD6, $SAD_2O$, SAD100, SAD500, SAD2000 (Xantec), SuperAvidin (Array-It), streptavidin slide (catalog #MPC 000, Xenopore) and STREPTAVIDINnslide (catalog #439003, Greiner Bio-one).

In certain embodiments, the first portion of the macromolecule can comprise a nucleotide sequence that is capable of selectively binding a nucleotide sequence on the substrate.

In further embodiments, the first portion of the macromolecule can comprise avidin, and the substrate can comprise biotin. Useful substrates comprising biotin are commercially available including Optiarray-biotin (Accler8), BD6, BD20, BD100, BD500 and BD2000 (Xantec).

Figure 2B:
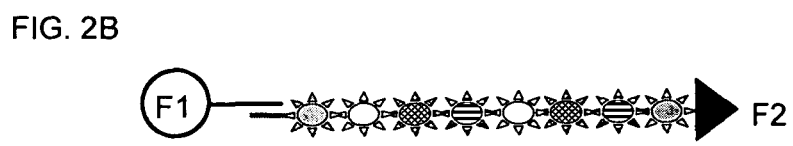
Figure 2C:
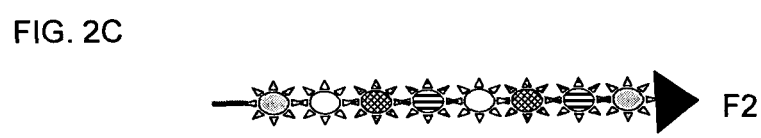

In further embodiments, the first portion of the macromolecule is capable of forming a complex with one or more other molecules that, in turn, are capable of binding, covalently or non-covalently, a binding moiety of the substrate. For instance, a first portion of the macromolecule can be capable of selectively binding another molecule that comprises, for instance, a biotin moiety that is capable of selectively binding, for instance, an avidin moiety of the substrate. FIG. 2A illustrates a macromolecule that is capable of selectively binding a second molecule X that is capable of selectively binding a third molecule that comprises F1. F1 is capable of selectively binding a moiety on a substrate. FIG. 2B illustrates a macromolecule that is capable of selectively binding a second molecule that comprises F1, and F1 is capable of selectively binding a moiety on a substrate.

In further embodiments, the first portion of the macromolecule can comprise a member of a binding pair that is capable of reacting with a member of a binding pair on the substrate to form one or more covalent bonds. Useful substrates comprising reactive groups include those that comprise a reactive moiety selected from the group consisting of succinamides, amines, aldehydes, epoxies and thiols. Exemplary useful substrates comprising reactive moieties include, but are not limited to, surfaces comprising epoxy, aldehyde, gold, hydrazide, sulfhydryl, NHS-ester, amine, thiol, carboxylate, maleimide, hydroxymethyl phosphine, imidoester, isocyanate, hydroxyl, pentafluorophenyl-ester, psoralen, pyridyl disulfide or vinyl sulfone, or mixtures thereof. Such surfaces can be obtained from commercial sources or prepared according to standard techniques. The first portion of the macromolecule would comprise a reactive moiety capable of reacting with the reactive moiety of the substrate. Exemplary useful substrates comprising reactive moieties include, but are not limited to, OptArray-DNA NHS group (Accler8), Nexterion Slide AL (Schott) and Nexterion Slide E (Schott).

In certain embodiments, the first portion of the macromolecule can comprise a reactive moiety that is capable of being bound to the substrate by photoactivation. The substrate could comprise the photoreactive moiety, or the first portion of the macromolecule could comprise the photoreactive moiety. Some examples of photoreactive moieties include aryl azides, such as N-((2-pyridyldithio)ethyl)-4-azidosalicylamide; fluorinated aryl azides, such as 4-azido-2,3,5,6-tetrafluorobenzoic acid; benzophenone-based reagents, such as the succinimidyl ester of 4-benzoylbenzoic acid; and 5-Bromodeoxyuridine.

In further embodiments, the first portion of the macromolecule can be immobilized to the substrate via other binding pairs apparent to those of skill in the art.

5.2.3 Extension of the Macromolecule

In certain methods of the invention, the macromolecule is in an extended state. Generally, any macromolecule is in an extended state if it would be recognized as such by one of skill in the art.

In certain embodiments, the macromolecule is in an extended state when it is in the field of a force capable of extending the macromolecule under conditions suitable for extending the macromolecule. Such forces and conditions should be apparent to those of skill in the art. For instance, many macromolecules can be extended by hydrodynamic force or by gravity, and many charged macromolecules can be extended by electromagnetic force. In certain embodiments, the force can be applied to the macromolecule indirectly. For instance, the macromolecule can comprise or can be linked, covalently or noncovalently, to a moiety capable of being moved by a force. In certain embodiments, the macromolecule can be linked to a moiety capable of being moved by electromagnetic, hydrodynamic or optical force.

In certain embodiments, the force is an electromagnetic force. For instance, when the macromolecule is charged, such as a polynucleotide, the macromolecule can be extended in an electric or magnetic field. The field should be strong enough to extend the macromolecule according to the judgment of one of skill in the art. Exemplary techniques for extending a macromolecule in an electric or magnetic field are described in Matsuura et al., 2002, *J Biomol Struct Dyn.* 20(3):429-36; Ferree & Blanch, 2003, *Biophys J.* 85(4):2539-46; Stigter & Bustamante, 1998, *Biophys J.* 1998 75(3):1197-210; Matsuura et al., 2001, *Nucleic Acids Res.* 29(16); Ferree & Blanch, 2004, *Biophys J.* 87(1):468-75; the contents of which are hereby incorporated by reference in their entirety.

In certain embodiments, the force is a hydrodynamic force. For instance, many macromolecules, including polysaccharides, polypeptides, and polynucleotides, can be extended in the field of a moving fluid. The hydrodynamic force should be strong enough to extend the macromolecule according to the judgment of one of skill in the art. Exemplary techniques for extending a macromolecule in hydrodynamic field are described in Bensimon et al., 1994, *Science* 265:2096-2098; Henegariu et al., 2001, *BioTechniques* 31: 246-250; Kraus et al., 1997, *Human Genetics* 99:374-380; Michalet et al., 1997, *Science* 277:1518-1523; Yokota et al., 1997, *Nucleic Acids Res.* 25(5):1064-70; Otobe et al., 2001, *Nucleic Acids Research* 29:109; Zimmerman & Cox, 1994, *Nucleic Acids Res.* 22(3):492-7, and U.S. Pat. Nos. 6,548,255, 6,344,319, 6,303,296, 6,265,153, 6,225,055, 6,054,327, 5,840,862, the contents of which are hereby incorporated by reference in their entirety.

In certain embodiments, the force is gravity. In advantageous embodiments, the force of gravity can be combined with, for example, hydrodynamic force to extend the macromolecule. In certain embodiments, The force should be strong enough to extend the macromolecule according to the judgment of one of skill in the art. Exemplary techniques for extending a macromolecule with gravity are described in Michalet et al., 1997, *Science* 277:1518-1523; Yokota et al., 1997, *Nucleic Acids Res.* 25(5):1064-70; Kraus et al., 1997, *Human Genetics* 99:374-380, the contents of which are hereby incorporated by reference in their entirety.

In particular embodiments, the force is applied through a moving meniscus. Those of skill in the art will recognize that a moving meniscus can apply various forces to a macromolecule including hydrodynamic force, surface tension and/or any other force recognized by those of skill in the art. The meniscus can be moved by any technique apparent to those of skill in the art including evaporation and gravity. Exemplary techniques for extending a macromolecule with a moving meniscus are described in, for example, U.S. Pat. Nos. 6,548,255, 6,344,319, 6,303,296, 6,265,153, 6,225,055, 6,054,327, 5,840,862, the contents of which are hereby incorporated by reference in their entireties.

In particular embodiments, the macromolecule can be extended by an optical trap or optical tweezers. For instance, the macromolecule can comprise or can be linked, covalently or noncovalently, to a particle capable of being trapped or moved by an appropriate source of optical force. Useful techniques for moving particles with optical traps or optical tweezers are described in Ashkin et al., 1986, *Optics Letters* 11:288-290; Ashkin et al., 1987, *Science* 235:1517-1520; Ashkin et al., *Nature* 330:769-771; Perkins et al., 1994, *Science* 264:822-826; Simmons et al., 1996, *Biophysical Journal* 70:1813-1822; Block et al., 1990, *Nature* 348:348-352; and Grier, 2003, *Nature* 424: 810-816; the contents of which are hereby incorporated by reference in their entireties.

In certain embodiments, the macromolecule can be extended by combinations of the above forces that are apparent to those of skill in the art. In the examples, below, certain macromolecules are extended by a combination of an electric field and hydrodynamic force.

The macromolecule is extended when it would be recognized as extended by one of skill in the art according to standard criteria for extension of a macromolecule. In certain embodiments, the macromolecule is extended when it loses most of its tertiary structural features as recognized by those of skill in the art. In certain embodiments, the macromolecule is extended when it loses most of its secondary structural features as recognized by those of skill in the art. In certain embodiments, the macromolecule is extended when its primary structural features are detectable in sequence when imaged according to standard techniques. Exemplary imaging techniques are described in the examples below.

In certain embodiments, an extended state of a macromolecule can be recognized by comparing its hydrodynamic radius to its average hydrodynamic radius when free in dilute solution. For instance, in certain embodiments, a macromolecule, or portion thereof, is extended when its hydrodynamic radius is more than about double its average hydrodynamic radius in dilute solution. More quantitatively, R represents the hydrodynamic radius of the macromolecule, or portion thereof, and $<R>$ represents the average hydrodynamic radius of the macromolecule, or portion thereof, in dilute solution. The average $<R>$ should be calculated such that R for the macromolecule, or portion thereof, when unbound in dilute solution is less than $2<R>95\%$ of the time. In certain embodiments, a macromolecule, or portion thereof, is in an extended state when R is greater than $1.5<R>$, greater than $1.6<R>$, greater than $1.7<R>$, greater than $1.8<R>$, greater than 1.9<R>, greater than 2.0<R>, greater than 2.1<R>, greater than 2.2<R>, greater than 2.3<R>, greater than 2.4<R>, greater than 2.5<R> or greater than 3.0<R>. In particular embodiments, a macromolecule, or portion thereof, is in an extended state when R is greater than 2.0<R>.

5.2.4 Orientation of the Macromolecule

In certain methods of the invention, the macromolecule is in an oriented state. Generally, any macromolecule is in an oriented state if it would be recognized as such by one of skill in the art.

In certain embodiments, the macromolecule is in an oriented state when it is in the field of a force capable of orienting the macromolecule under conditions suitable for orienting the macromolecule. Such forces and conditions should be apparent to those of skill in the art.

In certain embodiments, the force is an electromagnetic force. For instance, when the macromolecule is charged, such as a polynucleotide, the macromolecule can be oriented in an electric or magnetic field. The field should be strong enough to orient the macromolecule according to the judgment of one of skill in the art. Exemplary techniques for orienting a macromolecule in an electric or magnetic field are described above.

In certain embodiments, the force is a hydrodynamic force. For instance, many macromolecules, including polysaccharides, polypeptides, and polynucleotides, can be oriented in the field of a moving fluid. The hydrodynamic force should be strong enough to orient the macromolecule according to the judgment of one of skill in the art. Exemplary techniques for orienting a macromolecule in hydrodynamic field are described above.

In certain embodiments, the force is gravity. In advantageous embodiments, the force of gravity can be combined with, for example, hydrodynamic force or surface tension to orient the macromolecule. In certain embodiments, The force should be strong enough to orient the macromolecule according to the judgment of one of skill in the art. Exemplary techniques for orienting a macromolecule with gravity are described above.

In certain embodiments, the force in an optical force. For instance, the macromolecule can comprise or can be linked, covalently or noncovalently, to a particle capable of being trapped or moved by an appropriate source of optical force as described above.

In certain embodiments, the macromolecule can be oriented by combinations of the above forces that are apparent to those of skill in the art. In the examples, below, certain macromolecules are oriented by a combination of an electric field and hydrodynamic force.

The macromolecule is oriented when it would be recognized as oriented by one of skill in the art according to standard criteria for orientation of a macromolecule. In certain embodiments, the macromolecule is oriented when it is arranged in parallel, as recognized by those of skill in the art, with the field of a force capable of orienting the macromolecule. In certain embodiments, the macromolecule is oriented when it is one of a plurality of macromolecules that are arranged in parallel, as recognized by those of skill in the art. For instance, a plurality of macromolecules can be oriented when the vector from a first terminus to a second terminus of a macromolecule is parallel, as recognized by those of skill in the art, to the vectors between corresponding termini of other macromolecules in the plurality.

5.2.5 Selective Immobilization of Second Portion of Macromolecule

As discussed above, in the methods of the invention, a second portion of the macromolecule is selectively immobilized. The second portion of the macromolecule can be any portion of the macromolecule that is not identical to the first portion of the macromolecule. In some embodiments, the second portion of the macromolecule does not overlap any part of the first portion of the macromolecule.

In certain embodiments, the present invention provides methods that comprise the single step of selectively immobilizing a second portion of a macromolecule while the macromolecule is in an extended or oriented state, and while a first portion of the macromolecule is immobilized. Exemplary methods for immobilization of the first portion of the macromolecule, and for extension or orientation of the macromolecule are described in detail in the sections above.

In certain embodiments, the present invention provides methods that comprise the step of extending a macromolecule, while a first portion of the macromolecule is immobilized, and the step of selectively immobilizing a second portion of a macromolecule while the macromolecule is in an extended state. Exemplary methods for immobilization of the first portion of the macromolecule, and for extension of the macromolecule are described in detail in the sections above.

In certain embodiments, the present invention provides methods that comprise the step of immobilizing a first portion of a macromolecule, the step of extending the macromolecule while the first portion is immobilized and the step of selectively immobilizing a second portion of a macromolecule while the macromolecule is in an extended state. Exemplary methods for immobilization of the first portion of the macromolecule, and for extension of the macromolecule are described in detail above.

In certain embodiments, the present invention provides methods that comprise the step of orienting a macromolecule, while a first portion of the macromolecule is immobilized, and the step of selectively immobilizing a second portion of a macromolecule while the macromolecule is in an oriented state. Exemplary methods for immobilization of the first portion of the macromolecule, and for orienting the macromolecule are described in detail in the sections above.

In certain embodiments, the present invention provides methods that comprise the step of immobilizing a first portion of a macromolecule, the step of orienting the macromolecule while the first portion is immobilized and the step of selectively immobilizing a second portion of a macromolecule while the macromolecule is in an oriented state. Exemplary methods for immobilization of the first portion of the macromolecule, and for orienting the macromolecule are described in detail above.

The selective immobilization of the second portion of the macromolecule can follow any technique for selective immobilization of a macromolecule apparent to those of skill in the art. Significantly, in advantageous embodiments of the invention, the second portion of the macromolecule is not immobilized non-selectively. Selective immobilization can allow the macromolecule to be immobilized while in a fully extended state or nearly fully extended state. Selective immobilization can also allow the macromolecule to be immobilized in an oriented manner. In other words, the first portion and second portion of the macromolecule can be immobilized along the direction of the field or fields used to extend the macromolecule, with the first portion preceding the second portion in the field. When a plurality of macromolecules are immobilized, the can be uniformly oriented along the field.

The second portion of the macromolecule can be at any location in the macromolecule. In certain embodiments, the second portion is at a terminus of the macromolecule. In certain embodiments, the second portion is not at a terminus of the macromolecule. In certain embodiments, the first portion, described in the sections above, is at one terminus of the macromolecule, and the second portion is at another terminus of the macromolecule.

As discussed above, the second portion of the macromolecule is immobilized selectively. The immobilization can be by any selective interaction with the substrate apparent to those of skill in the art. The immobilization can be via electrostatic or ionic interaction, via one or more covalent bonds, via one or more non-covalent bonds or combinations thereof. In certain embodiments, the immobilization can be via electrostatic interaction with an electrode. In further embodiments, the immobilization is via electrostatic interaction with a substrate other than the electrode.

If the first portion and the second portion of the macromolecule are selectively immobilized to the same substrate, the techniques of selective immobilization should of course be compatible with the substrate. In particular embodiments, the techniques of immobilization are the same. For instance, on a substrate coated with avidin, both the first and second portion of the macromolecule can be immobilized selectively via biotin-avidin interactions. However, as will be apparent to those of skill in the art, the same interaction need not be used at both the first and second portions for immobilization on the same substrate. For instance, the substrate can comprise multiple moieties capable of selective binding, or the first portion can be immobilized non-selectively, or other techniques apparent to those of skill in the art.

In certain embodiments, the second portion of the macromolecule comprises a first member of a binding pair. The second member of the binding pair can be covalently bound to the second portion of the macromolecule, or they can be non-covalently bound. Useful covalent bonds and non-covalent bonds will be apparent to those of skill in the art. In useful embodiments, the substrate onto which the second portion of the macromolecule is bound will comprise a second member of the binding pair. The substrate can be covalently bound to the second member, or they can be non-covalently bound.

In certain embodiments, the second portion of the macromolecule can comprise a member of a binding pair that is capable of binding with a member of a binding pair on the substrate to form one or more non-covalent bonds. Exemplary useful substrates include those that comprise a binding moiety selected from the group consisting of ligands, antigens, carbohydrates, nucleic acids, receptors, lectins, and antibodies such as those described in the sections above.

In advantageous embodiments, the second portion of the macromolecule can be immobilized to the substrate via an avidin-biotin binding pair. In certain embodiments, the macromolecule can comprise a biotin moiety in its first portion. For instance, a polynucleotide macromolecule can comprise a biotinylated nucleotide residue. Similarly, a polypeptide macromolecule can comprise a biotinylated amino acid residue. Useful substrates comprising avidin are described in the sections above.

In further embodiments, the second portion of the macromolecule can comprise avidin, and the substrate can comprise biotin. Useful substrates comprising biotin are described in the sections above.

In further embodiments, the second portion of the macromolecule can comprise a member of a binding pair that is capable of reacting with a member of a binding pair on the substrate to form one or more covalent bonds. Exemplary useful substrates comprising reactive groups are described in the sections above.

In certain embodiments, the second portion of the macromolecule can comprise a reactive moiety that is capable of being bound to the substrate by photoactivation. The substrate could comprise the photoreactive moiety, or the second portion of the macromolecule could comprise the photoreactive moiety. Some examples of photoreactive moieties include aryl azides, such as N-((2-pyridyldithio)ethyl)-4-azidosalicylamide; fluorinated aryl azides, such as 4-azido-2,3,5,6-tetrafluorobenzoic acid; benzophenone-based reagents, such as the succinimidyl ester of 4-benzoylbenzoic acid; and 5-Bromo-deoxyuridine.

In further embodiments, the second portion of the macromolecule can be immobilized to the substrate via other binding pairs described in the sections above.

Figure 1B:
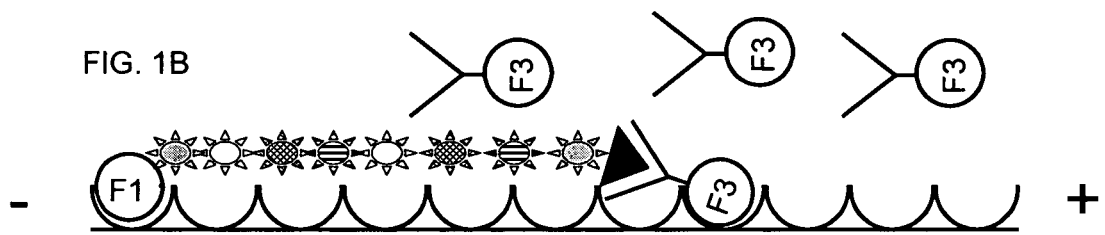

In further embodiments, the second portion of the macromolecule is capable of forming a complex with one or more other molecules that, in turn, are capable of binding, covalently or non-covalently, a binding moiety of the substrate. For instance, the second portion of the macromolecule can be capable of selectively binding another molecule that comprises, for instance, a biotin moiety that is capable of selectively binding, for instance, an avidin moiety of the substrate. FIG. 1B illustrates a macromolecule of selectively binding a second molecule that comprises F3 that is, in turn, capable of selectively binding a moiety on a substrate. The interaction between the second portion of the macromolecule and the molecule that comprises F3 can be mediated, for example, by an antigen-antibody interaction.

Figure 3A:
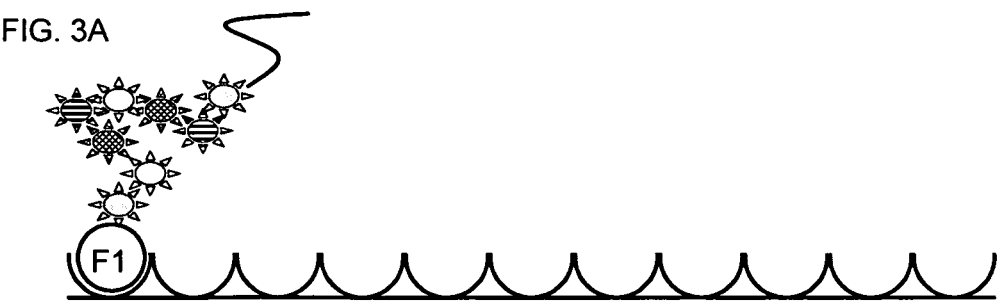
Figure 3B:
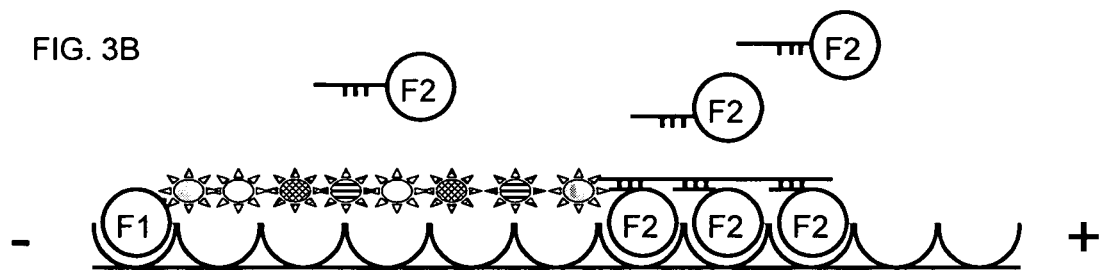
Figure 3C:
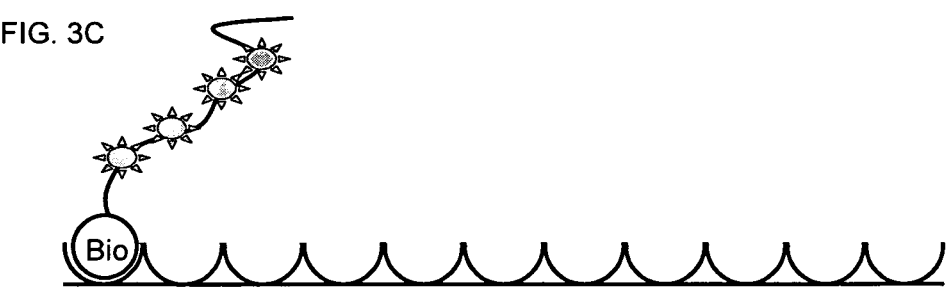
Figure 3D:
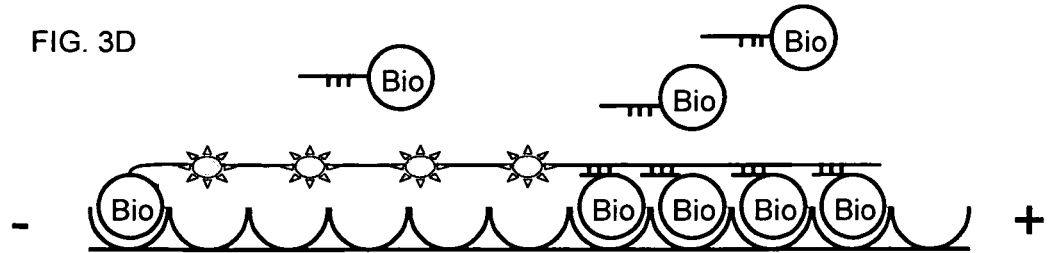

FIGS. 3A and 3B illustrate the selective immobilization of a macromolecule according to methods of the present invention. In FIG. 3A, a first portion of the macromolecule comprises binding moiety F1 that is capable of selectively binding a moiety on the illustrated substrate S. Binding moiety F1 can be, for instance, biotin, and substrate S can be coated with, for instance, avidin. The macromolecule of FIG. 3A is extended by a force as described in the sections above. In FIG. 3B, the force is an electrical potential. While extended, the macromolecule is contacted with molecules comprising binding moiety F2 that is capable of selectively binding a moiety on the illustrated substrate S. Binding moiety F2 can be, for instance, biotin, and substrate S can be coated with, for instance, avidin. Significantly, up to three molecules comprising F2 are capable of selectively binding a second portion of the macromolecule to selectively immobilize it in its extended state. As illustrated, the molecules comprise a second binding moiety that selectively binds a repeated binding moiety of the macromolecule. The binding moieties can be, for instance, complementary nucleic acid sequences, as illustrated in FIG. 3B. The resulting macromolecule is selectively immobilized in an extended state and should remain extended even when the force is removed. The selectively immobilized, extended macromolecule can be used for any purpose apparent to those of skill in the art.

5.2.6 Immobilization of Two Portions of an Extended or Oriented Macromolecule In certain embodiments, the present invention provides methods for selective immobilization of a first portion and a second portion of a macromolecule that is in an extended or oriented state. Significantly, according to these methods of the invention, the macromolecule need not be immobilized prior to application of a force capable of extending or orienting the macromolecule.

In these methods, the macromolecule is extended or oriented, or both, by a force capable of extending or orienting the macromolecule. Such forces are described in detail in the sections above. In particular embodiments, the force is a force capable of extending or orienting the macromolecule while maintaining the macromolecule in one location, i.e. a force capable of extending or orienting without substantially moving the macromolecule. Exemplary forces include oscillating electromagnetic fields and oscillating hydrodynamic fields. In a particular embodiment, the force is an oscillating electrical field. Exemplary techniques for extending or orienting a macromolecule in an oscillating electric field are described in Asbury et al., 2002, *Electrophoresis* 23(16):2658-66; Kabata et al., 1993, *Science* 262(5139):1561-3; and Asbury and van den Engh, 1998, *Biophys J.* 74:1024-30, the contents of which are hereby incorporated by reference in their entirety.

In the methods, the macromolecule is immobilized at a first portion and at a second portion while extended or oriented. Both the first portion and the second portion can be immobilized non-selectively, both can be immobilized selectively, or one can be immobilized selectively and the other non-selectively. Techniques for immobilization of the first portion and second portion are described in detail in the sections above.

5.2.7 Substrate for Immobilization

In the methods of the invention, the substrate for immobilization can be any substrate capable of selectively binding the macromolecule apparent to those of skill in the art. Further, in certain aspects, the present invention provides compositions comprising a selectively immobilized macromolecule in an extended state. The compositions comprise a substrate, as described herein, having immobilized thereto a macromolecule in an extended state. The macromolecule can be, of course, immobilized according to a method of the invention.

The only requirement of the substrate is that it be capable of selectively binding the second portion of the macromolecule as described above. Thus, the substrate can be a filter or a membrane, such as a nitrocellulose or nylon, glass, a polymer such as polyacrylamide, a gel such as agarose, dextran, cellulose, polystyrene, latex, or any other material known to those of skill in the art to which capture compounds can be immobilized. The substrate can be composed of a porous material such as acrylic, styrene methyl methacrylate copolymer and ethylene/acrylic acid.

The substrate can take on any form so long as the form does not prevent selective immobilization of the second portion of the macromolecule. For instance, the substrate can have the form of a disk, slab, strip, bead, submicron particle, coated magnetic bead, gel pad, microtiter well, slide, membrane, frit or other form known to those of skill in the art. The substrate is optionally disposed within a housing, such as a chromatography column, spin column, syringe barrel, pipette, pipette tip, 96 or 384 well plate, microchannel, capillary, etc., that aids the flow of liquid over or through the substrate.

The macromolecule can be immobilized on a single substrate or on a plurality of substrates. For instance, in certain embodiments, the first and second portions of macromolecule are immobilized on the same substrate, as recognized by those of skill in the art. In certain embodiments, the first portion of the macromolecule can be immobilized on a first substrate while the second portion of the macromolecule can be immobilized on a second substrate, distinct from the first.

The substrate can be prepared according to any method apparent to those of skill in the art. For a review of the myriad techniques that can be used to activate exemplary substrates of the invention with a sufficient density of reactive groups, see, the *Wiley Encyclopedia of Packaging Technology*, 2d Ed., Brody & Marsh, Ed., "Surface Treatment," pp. 867 874, John Wiley & Sons (1997), and the references cited therein. Chemical methods suitable for generating amino groups on silicon oxide substrates are described in Atkinson & Smith, "Solid Phase Synthesis of Oligodeoxyribonucleotides by the Phosphite Triester Method," In: *Oligonucleotide Synthesis: A Practical Approach*, M J Gait, Ed., 1984, IRL Press, Oxford, particularly at pp. 45 49 (and the references cited therein); chemical methods suitable for generating hydroxyl groups on silicon oxide substrates are described in Pease et al., 1994, *Proc. Natl. Acad. Sci. USA* 91:5022 5026 (and the references cited therein); chemical methods for generating functional groups on polymers such as polystyrene, polyamides and grafted polystyrenes are described in Lloyd Williams et al., 1997, Chemical Approaches to the Synthesis of Peptides and Proteins, Chapter 2, CRC Press, Boca Raton, Fla. (and the references cited therein).

Exemplary useful substrates include surfaces coated with streptavidin, e.g. Accelr8 TB0200. Further useful substrates include surfaces coated with N-hydroxysuccinamide that are capable of reacting with a portion of a macromolecule that comprises an amine. One such surface is OptArray-DNA (Accelr8). Additional useful surfaces are coated with aldehyde (e.g. Nexterion Slide AL, Schott) and surfaces coated with epoxy (e.g. Nexterion Slide E, Schott). Another useful surface is a biotinylated BSA coated surface useful for selective immobilization of a portion of a macromolecule that comprises avidin or streptavidin.

5.3 Methods of Using Selectively Immobilized, Extended or Oriented Macromolecules The selectively immobilized, extended and/or oriented macromolecules can be used for any purpose apparent to those of skill in the art. For instance, the selectively immobilized, extended and/or oriented macromolecules are useful for mapping, nanoassembly and surface plasmon resonance.

In certain embodiments, the selectively immobilized, extended and/or oriented macromolecules can be used for macromolecular with a variety of techniques, e.g., atomic force microscopy or electron microscopy.

In certain embodiments, the selectively immobilized, extended and/or oriented macromolecules can be used for macromolecular mapping. For instance, they can be used to determine the location of binding or hybridization along a macromolecule by, for example, fluorescent molecules or DNA binding proteins.

In certain embodiments, the selectively immobilized, extended and/or oriented macromolecules can be used for nanoassembly. For instance, they can be used to faciliate crystal growth on extended and/or oriented macromolecules, or crystal growth on polypeptides linked or bound to extended and/or oriented macromolecules. In certain embodiments, the selectively immobilized, extended and/or oriented macromolecules can be used for the construction of nanopaths. In certain embodiments, the selectively immobilized, extended and/or oriented macromolecules can be used for directed transport using molecular motors, such as kinesin or myosin. In certain embodiments, the selectively immobilized, extended and/or oriented macromolecules can be used for molecular computing or for the assembly of circuits comprising macromolecules, i.e. DNA computing. In certain embodiments, the selectively immobilized, extended and/or oriented macromolecules can be used to manipulate carbon nanotubes.

In certain embodiments, the selectively immobilized, extended and/or oriented macromolecules can be used for the study of polynucleotide binding proteins. They can be used, for instance, to determine the presence or location of protein bound to a polynucleotide. Useful techniques include surface plasmon resonance.

In certain embodiments, the selectively immobilized, extended and/or oriented macromolecules can be used for the study of protein fibers, such as amyloid, titin, and fibronectin.

In certain embodiments, the selectively immobilized, extended and/or oriented macromolecules can be used to create macromolecular barcodes for the purposes of separation and sequential detection of labels. These labels spaced along the molecule provide a unique code that can be read when the macromolecule is immobilized and extended and/or oriented. Extension and/or orientation with selective immobilization can facilitate the decoding of the macromolecular barcode.

The selectively immobilized, extended and/or oriented macromolecules can further be used for can be used in any context where detection or imaging of a macromolecule might be useful. They can be used for diagnostic, prognostic therapeutic and screening purposes. For instance, they can be applied to the analysis of biomolecular samples obtained or derived from a patient so as to determine whether a diseased cell type is present in the sample and/or to stage the disease. They can be used to diagnose pathogen infections, for example infections by intracellular bacteria and viruses, by determining the presence and/or quantity of markers of bacterium or virus, respectively, in the sample. The compositions and methods of the invention can be used to quantitate target molecules whose abundance is indicative of a biological state or disease condition, for example, blood markers that are upregulated or downregulated as a result of a disease state. In addition, the compositions and methods of the invention can be used to provide prognostic information that assists in determining a course of treatment for a patient.

5.4 Kits Comprising Selectively Immobilized, Extended or Oriented Macromolecules The invention further provides kits comprising one or more components of the invention. The kits can comprise, for example, a substrate according to the invention and one or more extended and/or oriented, or both, macromolecules selectively immobilized on the substrate. The kits can be used for any purpose apparent to those of skill in the art, including, those described above.

In certain embodiments, the present invention also provides kits useful for the extension and/or orientation and selective immobilization of macromolecules. The kits can comprise a substrate for immobilization and one or more binding partners to facilitate extension and/or orientation or immobilization of a macromolecule. The binding partners could, in certain embodiments, comprise a moiety useful for extension and/or orientation of the macromolecule in an appropriate force. In certain embodiments, the binding partners could facilitate immobilization or selective immobilization of the macromolecule to the surface. In further embodiments, the kit could comprise a macromolecule for extension and/or orientation and immobilization. In further embodiments, the kit could comprise a device capable of extending the macromolecule.

In certain embodiments, the present invention provides kits comprising a container and one or more components of the kits described above.

The following examples are offered to illustrate this invention and are not to be construed in any way as limiting the scope of this invention.

6. EXAMPLES

6.1 Example 1

Selective Immobilization of Extended DNA

A double stranded RNA-DNA hybrid 7.2 Kb in length is functionalized at one terminus with biotin. At the other terminus, the DNA comprises a single stranded sequence of 15 bases repeated 4 times (5'-GTC TAT CAT CAC AGC GTC TAT CAT CAC AGC GTC TAT CAT CAC AGC GTC TAT CAT CAC AGC-3'; SEQ ID NO:1). Thus, the DNA comprises four binding sites at one terminus for selective immobilization. The hybrid also has 4 regions with Cy3 fluorophores incorporated into the RNA.

Figure 4A:
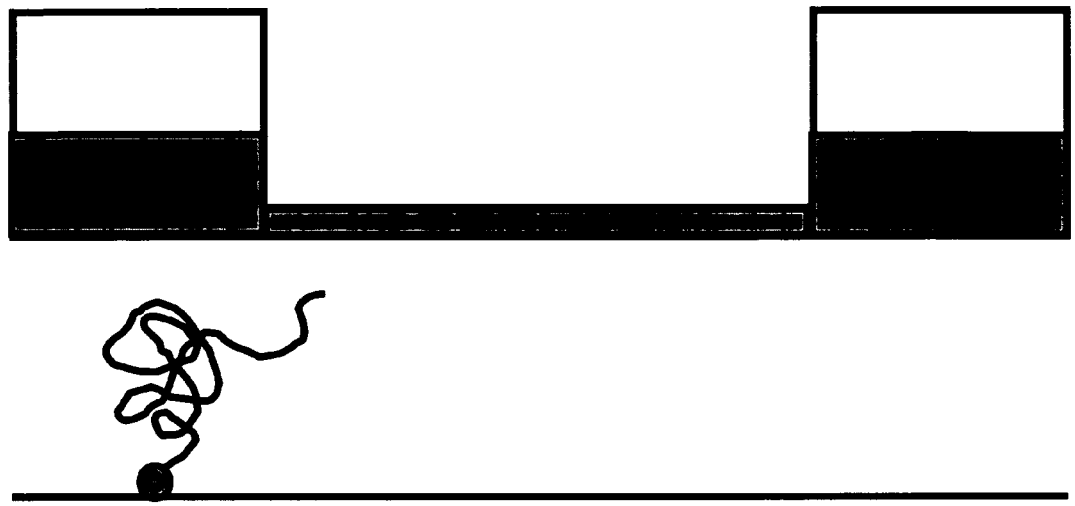
FIG. 4A illustrates immobilization of one terminus of a DNA molecule in a microfluidic device.

A small sample of the DNA (3 µL, 0.01 fmol/µL in 1×TAE, or 40 mM Tris acetate, 1 mM EDTA, pH 8.0) is transferred into a microfluidic device comprising a channel molded into polydimethylsiloxane that is passively adhered to a streptavadin coated coverslip (Accelr8, TB0200). The channel dimensions are 50 µm×1 mm×10 mm. See FIG. 4A. The sample is contacted with the coverslip at room temperature for 15 minutes allowing the DNA to selectively bind the streptavadin surface via the biotin at the terminus of the DNA. Unbound DNA is washed away by fluid flow. The 1×TAE buffer in the wells are exchanged for fresh buffer and fluid levels are evened out at 30 µL each well. See FIG. 4A.

Figure 4B:
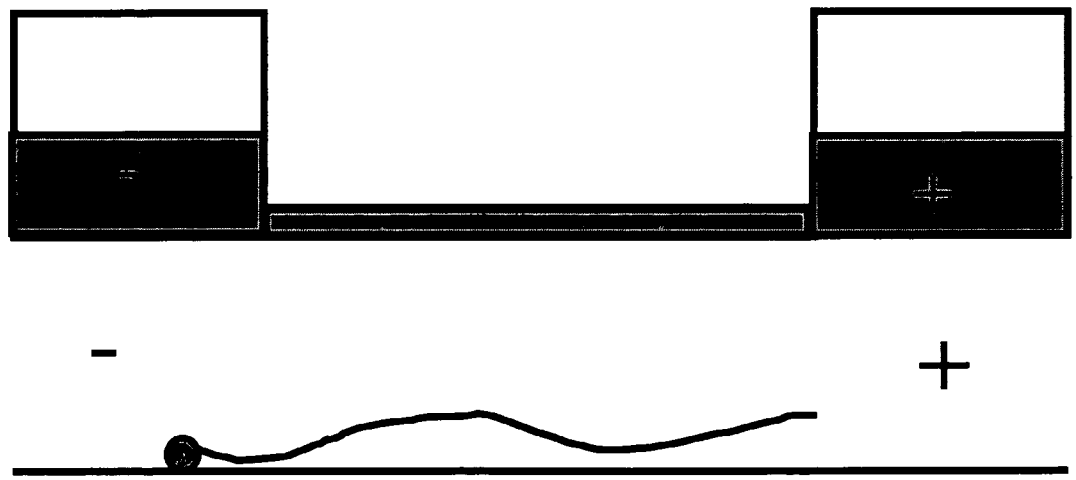
FIG. 4B illustrates extension of the DNA in an electric field.

An electric field of 200 V/cm is applied to extend the long negatively charged DNA (see FIG. 4B) toward the positive electrode.

Figure 4C:
FIG. 4C illustrates selective immobilization of a second terminus of the extended DNA molecule.
Figure 4C:

An immobilization agent, a biotinylated oligonucleotide (5'-\5Biotin\GCTGTGATGATAGAC-3' (SEQ ID NO:2), 50 µL @ 100 nM, 1×TAE) complementary to the second terminus of the DNA, is added to the negative well. The additional volume raises the fluid level in the well and induces hydrostatic flow to introduce the immobilization reagent into the channel (see FIG. 4C). The flow also acts to further stretch the DNA in addition to the electric field.

The biotinylated oligonucleotide hybridizes with the second terminus of the DNA while it is extended and selectively binds the streptavidin of the coverslip. The sample can be effectively immobilized in an extended state in less than 5 minutes.

6.2 Example 2

Imaging of Selectively Immobilized, Extended Macromolecules

A macromolecule comprising fluorophore labels and biotin affinity tags is prepared and purified according to Example 3. The macromolecule is bound to a coverslip surface comprising biotin and stretched with an electric field according to Example 3. Finally macromolecule is illuminated with an Arc lamp and imaged with a camera. An exemplary image is provided in FIG. 5. Individual dyes and, significantly, the order of those dyes on individual macromolecules can be detected in the image.

6.3 Example 3

Preparation and Imaging of Selectively Immobilized, Extended Macromolecules Herein is a step-by-step example of the construction of a nanoreporter from various components. It can be appreciated that various components can be constructed or added either at the same time, before or after other components. For example, annealing patch units or flaps to a scaffold can be done simultaneously or one after the other.

6.3.1 Scaffold Production

Single-stranded circular M13mp18 DNA (USB) is annealed to a 5-fold molar excess of an oligonucleotide complementary to the Bam HI recognition site (Bam Cutter oligo) and cut with Bam HI restriction enzyme to yield a linear single-stranded DNA backbone. An oligonucleotide complementary to the Bam Cutter oligonucleotide (anti-Bam oligonucleotide) is subsequently added in 50-fold excess to sequester free Bam Cutter oligonucleotide and thus prevent recircularization of the M13 during later steps.

The linear M13 molecule serves as a scaffold onto which RNA patches, or RNA segments, with incorporated fluorophores can be annealed.

6.3.2 PCR to Form Double-Stranded Positions on the M13 Scaffold

Ten sets of oligonucleotide primer pairs were designed to create 10 different regions along the M13 scaffold. Each pair contains one primer which has a T7 RNA polymerase promoter at the 5' end. Regions 2-7 are designed to be 900 bases (approximately 300 nm) long, as this is the approximate size of a diffraction-limited spot (the smallest spot that can be achieved with standard optics). Regions 1 and 8 have both long and short versions: the long versions cover the whole 900-base region, while the short versions cover only a portion of the 900-base region to allow a target-specific sequence to be ligated. Thus a target-specific sequence can be attached to either end. The ends can also be used for attachment of anchors or tags.

PCR is performed using Taq polymerase and 0.5 ng of double-stranded M13 mp 18 (USB) as a template. Reactions are cleaned up using a Qiaquick® purification kit from Qiagen. Each PCR reaction yields a double-stranded fragment corresponding to one specific segment as illustrated below. These fragments are used as templates for the in vitro transcription of the RNA segments.

6.3.3 In Vitro Transcription to Produce Dark RNA Segments

Using the PCR products described above as double-stranded templates, RNA segments are generated using an in vitro transcription kit from Ambion (Megascript® T7 kit). The products of the transcription reactions are purified (including treatment with DNAse I to remove template) using a RNeasy® Kit from Qiagen.

6.3.4 In Vitro Transcription to Produce RNA Segments Modified With Aminoallyl Groups Using the PCR products described above as double-stranded templates, RNA segments for later dye-coupling are generated using an in vitro transcription kit from Ambion (MessageAmp aRNA kit). Aminoallyl-modified UTP nucleotides are incorporated into the RNA segments during transcription. The products of the transcription reactions are purified (including treatment with DNAse I to remove template) using a RNeasy Kit from Qiagen.

6.3.5 Dye Coupling of Aminoallyl RNA Segments to Produce Colored Rna Segments 20-100 µg of aminoallyl-modified RNA segment is coupled with NHS-ester dyes using Ambion Aminoallyl Labeling Kit. Dyes used include Alexa Fluor® 488, Alexa Fluor® 594 and Alexa Fluor® 647 (Invitrogen/Molecular Probes) as well as Cy3 (Amersham).

Each segment is made separately in 4 colors so that each position on the scaffold can be filled with a segment in any of the four colors; thus different colors can be added at different positions to create many unique color combinations.

In this particular embodiment, adjacent segments must be of different colors or there may be dark segments interspersed so that each segment is detected as an individual 'spot'. Dark segments may be used as part of the nanoreporter code.

6.3.6 Assembly of the Label Molecule

Segments for each position are annealed in a 2:1 ratio of segment to M13 scaffold in 1×SSPE buffer at 70° C. for 2 hours.

An assembled nanoreporter with labeled RNA segments is depicted in FIG. 6A-6B. FIG. 6A depicts a nanoreporter in which only alternate "spots" (1, 3, 5 and 7) are labeled, and FIG. 6B depicts a nanoreporter in which every spot is labeled.

6.3.7 Synthesis of Probe and Target Oligonucleotides

S2 DNA target oligonucleotide was synthesized and purified by polyacrylamide gel electrophoresis (Integrated DNA Technologies). S2 RNA target molecules were generated by in vitro transcription of PCR products corresponding to region of cloned SARS coronavirus gene (Invitrogen) using an Ambion Megascript™ kit per manufacturer’s instructions. The S2 ghost probe (FIG. 8A (i) was complementary to a specific 50-base region of the S2 target sequence (S2-a) and was synthesized with a biotin-TEG monomer at the 5' end and purified by high performance liquid chromatography (Integrated DNA Technologies). A second oligonucleotide with 50 bps complementary to the S2 target (S2-b) plus 9 bp of a additional sequence used for ligation to the M13 scaffold (59 bp total) was synthesized and purified by HPLC (Integrated DNA Technologies). Note that S2-a and S2-b target regions were not overlapping.

6.3.8 Nanoreporter Synthesis

Oligonucleotide S2-b was ligated to the 5' end of linearized M13 [FIG. 8A (iii)], and the resulting product was purified away from residual unligated oligonucleotide by size-exclusion filtration through a YM100 filter (Millipore) per manufacturer’s instructions. Amino-allyl-modified RNA segments complementary to M13 is positions 2, 4, 6, and 8 (FIG. 7A) were generated from in vitro-transcription of DNA templates (PCR products) via the Ambion Megascript™ kit per manufacturer’s instructions. The segments were then coupled to NHS-ester-modified Alexa Fluor® 647 dye (Invitrogen) per Ambion’s instructions (amino allyl MessageAmp™ II aRNA kit). RNA segments corresponding to positions 1, 3, 5, and 7 of the M13 scaffold (FIG. 7C) were generated as unmodified in vitro-transcribed RNAs from DNA templates as described above. Assembly of the nanoreporter was carried out by annealing 10 fmol/μl of each of the eight segments to 5 fmol/.mu.l of the M13-S1-b scaffold for 2 hours at 70° C. in 1×SSPE buffer (150 mM sodium chloride, 10 mM sodium phosphate, 1 mM EDTA). The final product was a nanoreporter with 4 segments labeled with A647 (red) interspersed with dark segments.

6.3.9 Hybridization Conditions

Hybridization of nanoreporters and ghost probes to target were carried out under the following conditions: 5×SSPE (750 mM sodium chloride, 50 mM sodium phosphate, 5 mM disodium EDTA), 40 pM ghost probe (attachment oligonucleotide S2-a), 40 pM Nanoreporter S2-b, 100 ng/μl sheared salmon sperm DNA, 5×Denhardt's solution and 0.1% Tween. Final target concentrations were 20 pM S2 DNA target (FIG. 8B) and 1 pM S2 RNA target (FIG. 8C). No target was added to the negative control (FIG. 8D). The hybridization reaction was incubated at 65° C. for at least 16 h.

Hybridization reactions were diluted 1:2 with 100 mM Borate buffer solution (pH 9.8) and introduced into a flow cell channel and bound to a streptavidin-coated coverslip forming the bottom of the channel (Streptavidin-OptiChem coverslips from Accelr8). Attachment to the slide by one end of the nanorerporter/target/ghost probe complex was achieved via interaction of the biotinylated ghost probe with the streptavidin surface. After rinsing the channel with additional borate buffer to remove excess reporters not bound to the surface, the buffer was exchanged with 1×TAE (40 mM Tris-acetate, 1 mM EDTA) and a current of 200V was applied to stretch out the nanoreporter/target complexes during image capture.

6.3.10 Surface Attachment

Once the nanoreporters are attached to both target molecule and corresponding labeled nucleic acids, i.e., nucleic acids attached to label monomers, they are attached to a surface and stretched in resolve the order of signals emitted by the label monomers and thus identify the target molecule. In this example, the nanoreporters are stretched to spatially resolve their fluorescent dye codes which correspond to a particular target molecule. The nanoreporters are stretched by attaching one end to a surface (in this example—a coverslip, see preparations below). Two methods for surface attachment may be used: A) streptavidin coated slides from Accelr8 Corporation with the nanoreporters being biotinylated and B) biotin coated slides with the nanoreporters having streptavidin. In buffer, the nanoreporters are brought into contact with the active surface and allowed to incubate for a period of time. The reaction is performed in flow cells which were made from PDMS molded in etched silicon wafers to make the channels. Metal tubing is used to core wells at the ends of the channels for buffer and sample insertion. Channel dimensions are 0.5 mm or 1 mm wide and 54 μm high. Once the sample has been loaded into the flow cell lane and incubated, the nanoreporters should be attached. Nanoreporters can be stretched either by applying a voltage or by removing the liquid with a receding meniscus leaving the strings stretched and dry.

6.3.11 Preparation of Surface and Assembly of Device

The binding surfaces (Accelr8 brand Streptavidin-OptiChem, coated coverslips) are shipped in units of 5 surfaces per slide container, and each container is enclosed with a package of silica dessicant in a foil pouch. The pouches are stored at −20° C. until use.

To prepare the surface for binding, a pouch is first pulled from the freezer and allowed to come to room temperature over several minutes. If previously unopened, the pouch is then sliced along one edge to form a slit, and the container of surfaces is removed. Upon removal of the required surface, the container is replaced in the pouch with its dessicant, the slit is sealed closed with a strip of packaging tape, and the pouch is replaced in the freezer.

The surface is then lightly rinsed with a stream of Nanopure water (Barnstead Nanopure Diamond) and soaked for 10 minutes in 0.2 μm-filtered 1×PBS in a clean, slotted Coplin jar. After soaking, the surface is dipped in Nanopure water and dried by blowing filtered nitrogen across the surface edge.

The PDMS device used to mate with the surface and provide localization of the sample is cleaned just before use by applying cellophane tape to the PDMS surface and then peeling away dust or other particles which may have become attached during storage. The binding side of the Accelr8 surface is laid face-up, and the clean PDMS structure is centered, channel side down, on the surface. PDMS adheres readily to coated glass, and no further attachment mechanism is necessary.

6.3.12 Sample Binding and Washing

The sample is bound to the surface by first applying a 5 μL drop of the sample (currently diluted in 100 mM sodium borate buffer, pH 9.8) in one well of the chosen lane. The drop should just touch the point at which the channel joins the well (some sample may wick into the channel at this point). The channel is filled, and binding is equalized throughout the channel, by pulling the droplet through the channel to the opposite well using a very weak vacuum (<2 kPa). The process is repeated for the other samples in their respective lanes. Excess fluid is then removed from the wells, the wells are taped to reduce evaporation, and the device is incubated at room temperature in the dark for 20 minutes.

After binding, the tape is removed, and the top well of each lane is filled with 100 μL of the borate buffer described above. About 20 μL of that buffer is pulled through the channels to the other wells using the vacuum, and the process is repeated once. All borate buffer is then removed from all wells, and the top well is filled with 1×TAE, pH 8.3. About 50 μL TAE is pulled through the channel, then all TAE is removed and the well is refilled. The process is repeated three times, for a total of about 150 μL of TAE rinse. Finally, all wells are filled with 100 μL 1×TAE.

6.3.13 Electrostretching

The bottom of the coverslip/PDMS device is spotted with immersion oil and placed on the microscope. Electrodes are inserted into the wells on opposite ends of the first PDMS channel (negative electrode in top well, positive in bottom). The first image of the channel will be taken close to the bottom well; the microscope stage is adjusted so that the area of interest is in focus.

Voltage (200 V) is then applied across the channel. Voltage is supplied by a DC power supply (Agilent E3630A) and amplified 100× through a amplified by a high voltage amplifier (Matsusada Precision Inc.). After the current is applied, focus is readjusted, and the imaging process begins.

The electrostretching and imaging process is then repeated with the remaining channels. Image the nanoreporters.

6.3.14 Light Source for the Fluorescent Dyes on the Nanoreporter

In using an arc lamp as a light source, the best fluorophore selection is the brightest types without leading to fluorescent overlap such as Alexa Fluor® 488, Cy3, and Alexa Fluor® 594. Weaker fluorescent dyes such as Alexa Fluor® 647 and Cy5.5 may also be used.

6.3.15 Filters to Image the Fluorescent Dyes on the Nanoreporter

For the selected fluorophores Alexa Fluor® 488, Cy3, Alexa Fluor® 594 and Alexa Fluor® 647 there may be an overlap between the Cy3 and Alexa Fluor® 594. However, custom ordering an emission filter with a bandwidth of 572-600 nm minimizes the overlap.

6.3.16 Microscope and objective lens to image the nanoreporters

The microscope model used is the Nikon Eclipse TE2000E from Nikon Incorporation using the inverted fluorescence imaging station which has 6 filter cassettes that allow the selection of fluorescent emission from multiple fluorescent dye candidates. For the selected dyes, the optical resolution required is about 400 nm for all the wavelengths (500-700 nm). The selected objective lens is the Nikon Plan Apo TIRF lens which has a NA of 1.45 and magnification of 60. The optical resolution is ~210-300 nm for different wavelengths.

Five minutes before using the microscope (Nikon Eclipse TE2000E), turn on the light source (X-cite 120, Exfo Corporation) and make sure the intensity is the maximum. Turn on the CCD camera driver (Hamamatsu, Orca Ag) and the shutter controller. Use the oil objective of 60×1.45NA (Plan Apo TIRF, Nikon) to evaluate the nanoreporters. For all the nanoreporter evaluations the optivar is set at 1×. Open the Metamorph software (Universal Imaging Corporation). Acquire the images using the corresponding filter sets such as cy3, A647 (Chroma Technologies).

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for extending and selectively immobilizing a polynucleotide complex on a substrate comprising steps of:
    (a) providing a first nucleic acid molecule comprising:
        (i) a first target-specific sequence capable of binding to a target nucleic acid,
        (ii) a first label attachment region, which is non-overlapping with the first target-specific sequence, comprising a first DNA sequence hybridized to a first RNA molecule that is attached to one or more detectable labels that emit light which constitutes a first signal,
        (iii) a second label attachment region, which is non-overlapping with the first target-specific sequence and the first label attachment region, comprising a second DNA sequence hybridized to a second RNA molecule that is attached to one or more detectable labels that emit light which constitutes a second signal, and
        (iv) a first moiety that is capable of selectively binding to the substrate;

(b) providing a second nucleic acid molecule comprising:
  (i) a second target-specific sequence capable of binding to the target nucleic acid; wherein the first target-specific sequence and the second target-specific sequence bind to different regions of the target nucleic acid and
  (ii) a second moiety that is capable of selectively binding to the substrate;
(c) contacting the first nucleic acid molecule and the second nucleic acid molecule with a sample containing a target nucleic acid under conditions sufficient for hybridization of the first and the second nucleic acid molecules to the target nucleic acid, thereby producing the polynucleotide complex;
(d) selectively binding the first moiety to the substrate, thereby selectively immobilizing the first nucleic acid of the polynucleotide complex to the substrate;
(e) applying to the polynucleotide complex a force sufficient to extend the polynucleotide complex such that the first signal and the second signal are spatially separated;
(f) selectively binding the second moiety to the substrate, thereby selectively immobilizing the second nucleic acid of the polynucleotide complex to the substrate and thereby selectively immobilizing the extended polynucleotide complex to the substrate; and
(g) removing the force, with the polynucleotide complex remaining selectively immobilized in an extended state.

2. The method of claim 1, wherein the first nucleic acid molecule comprises additional label attachment regions which are non-overlapping with other label attachment regions.

3. The method of claim 2, wherein at least one of the additional label attachment regions comprises a DNA sequence hybridized to an RNA molecule that is attached to one or more detectable labels that emit light.

4. The method of claim 2, wherein at least one of the additional label attachment regions comprises a DNA sequence hybridized to an RNA molecule that is not attached to a detectable label that emits light.

5. The method of claim 2, wherein at least one of the additional label attachment regions comprises a DNA sequence hybridized to an RNA molecule that is attached to one or more detectable labels that emit light and at least another one of the additional label attachment regions comprises a DNA sequence hybridized to an RNA molecule that is not attached to a detectable label that emits light.

6. The method of claim 1, wherein the first nucleic acid molecule further comprises a third and a fourth label attachment regions, which are non-overlapping with the other label attachment regions, each comprising a DNA sequence hybridized to an RNA molecule that is attached to one or more detectable labels that emit light.

7. The method of claim 6, wherein the first nucleic acid molecule further comprises at least one additional label attachment region, which is non-overlapping with the other label attachment regions, comprising a DNA sequence hybridized to an RNA molecule that is not attached to a detectable label.

8. The method of claim 6, wherein the first nucleic acid molecule comprises at least three additional label attachment regions, which are non-overlapping with the other label attachment regions, each comprising a DNA sequence hybridized to an RNA molecule that is not attached to a detectable label.

9. The method of claim 8, wherein an additional label attachment region comprising a DNA sequence hybridized to an RNA molecule that is not attached to a detectable label is located between a pair of label attachment regions in which each member of the pair comprises a DNA sequence hybridized to an RNA molecule that is attached to one or more detectable labels.

10. The method of claim 9, wherein an additional label attachment region comprising a DNA sequence hybridized to an RNA molecule that is not attached to a detectable label is located between each pair of label attachment regions in which each member of the pair comprises a DNA sequence hybridized to an RNA molecule that is attached to one or more detectable labels.

11. The method of claim 1, wherein the force is a direct current electrical field.

12. The method of claim 1, wherein the first moiety or the second moiety selectively binds to the substrate via one or more non-covalent bonds.

13. The method of claim 1, wherein the first moiety or the second moiety selectively binds to the substrate via one or more covalent bonds.

14. The method of claim 1, wherein the force is sufficient to orient the polynucleotide complex.

15. The method of claim 14, wherein the extended polynucleotide complex is immobilized in an oriented state.

16. The method of claim 1, wherein the target nucleic acid is single stranded.

17. The method of claim 1, wherein the target nucleic acid comprises two complementary strands.

18. The method of claim 1, wherein the target nucleic acid is DNA or RNA.

19. The method of claim 1, wherein the first and second RNA molecules each comprise four or more aminoallyl-modified UTP nucleotides.

20. The method of claim 6, wherein the first and second RNA molecules and the RNA molecules hybridized to the third or the fourth label attachment regions each comprise four or more aminoallyl-modified UTP nucleotides.

21. The method of claim 19, wherein one or more fluorophore labels is attached to each aminoallyl-modified UTP nucleotide.

22. The method of claim 20, wherein one or more fluorophore labels is attached to each aminoallyl-modified UTP nucleotide.

23. The method of claim 1, wherein the first nucleic acid molecule or the second nucleic acid molecule hybridizes to a terminus of the target nucleic acid.

24. The method of claim 23, wherein the first nucleic acid molecule and the second nucleic acid molecules each hybridize to a terminus of the target nucleic acid.

25. The method of claim 1, wherein the first nucleic acid molecule or the second nucleic acid molecule hybridizes to a non-terminus of the target nucleic acid.

26. The method of claim 25, wherein the first nucleic acid molecule and the second nucleic acid molecules each hybridize to a non-terminus of the target nucleic acid.

27. The method of claim 1, wherein the first moiety and the second moiety are each selected from the group consisting of ligands, antigens, carbohydrates, nucleic acids, receptors, lectins, and antibodies.

28. The method of claim 1, wherein the first moiety or the second moiety are each selected from the group consisting of biotin, digoxigenin, FITC, avidin, streptavidin, antidigoxigenin, and anti-FITC.

29. The method of claim 1, wherein the first moiety or the second moiety are each selected from the group consisting of succinamides, amines, aldehydes, epoxies, and thiols.

30. The method of claim 1, wherein the substrate comprises a ligand, an antigen, a nucleic acid, a receptor, or an antibody.

31. The method of claim 30, wherein the substrate comprises biotin, digoxigenin, FITC, avidin, streptavidin, anti-digoxigenin, or anti-FITC.

32. The method of claim 1, wherein the substrate comprises succinamides, amines, aldehydes, epoxies, or thiols.

33. The method of claim 1, wherein the substrate is comprised of nitrocellulose, nylon, glass, a polymer, a gel, dextran, cellulose, or latex.

34. The method of claim 1, wherein the substrate is selected from the group consisting of a membrane, a bead, a filter, a porous material, and a glass surface.

35. The method of claim 34, wherein the membrane is comprised of nitrocellulose or nylon.

36. The method of claim 34, wherein the filter is comprised of nitrocellulose or nylon.

37. The method of claim 34, wherein the porous material is comprised of an acrylic, styrene methyl methacrylate copolymer, or ethylene/acrylic acid.

38. The method of claim 1, wherein the substrate comprises a form selected from the group consisting of a disk, a slab, a strip, a bead, a submicron particle, a coated magnetic bead, a gel pad, a microtiter well, a slide, a membrane, and a frit.

39. The method of claim 1, wherein the substrate is coated with streptavidin, biotinylated BSA, aldehyde, or epoxy.

* * * * *

SEQUENCE LISTING

```
<160> NUMBER OF SEQ ID NOS: 2

<210> SEQ ID NO 1
<211> LENGTH: 60
<212> TYPE: DNA
<213> ORGANISM: Artificial Sequence
<220> FEATURE:
<223> OTHER INFORMATION: a 15-bases repeats (4X) functioning as binding
      sites for selective immobilization

<400> SEQUENCE: 1
gtctatcatc acagcgtcta tcatcacagc gtctatcatc acagcgtcta tcatcacagc    60

<210> SEQ ID NO 2
<211> LENGTH: 15
<212> TYPE: DNA
<213> ORGANISM: Artificial Sequence
<220> FEATURE:
<223> OTHER INFORMATION: biotinylated oligonucleotide as an
      immobilization agent

<400> SEQUENCE: 2
gctgtgatga tagac                                                     15
```